(12) United States Patent  (10) Patent No.: US 9,241,720 B2
Forsell  (45) Date of Patent: Jan. 26, 2016

(54) HIP JOINT INSTRUMENT AND METHOD

(76) Inventor: Peter Forsell, Bouveret (CH)

( * ) Notice: Subject to any disclaimer, the term of this patent is extended or adjusted under 35 U.S.C. 154(b) by 830 days.

(21) Appl. No.: 13/382,840

(22) PCT Filed: Jul. 12, 2010

(86) PCT No.: PCT/SE2010/050823
§ 371 (c)(1),
(2), (4) Date: Jan. 6, 2012

(87) PCT Pub. No.: WO2011/005204
PCT Pub. Date: Jan. 13, 2011

(65) Prior Publication Data
US 2012/0109229 A1  May 3, 2012

Related U.S. Application Data

(60) Provisional application No. 61/299,738, filed on Jul. 30, 2009, provisional application No. 61/229,739,
(Continued)

(30) Foreign Application Priority Data

| Jul. 10, 2009 | (SE) | 0900957 |
| Jul. 10, 2009 | (SE) | 0900958 |
| Jul. 10, 2009 | (SE) | 0900959 |
| Jul. 10, 2009 | (SE) | 0900960 |
| Jul. 10, 2009 | (SE) | 0900962 |
| Jul. 10, 2009 | (SE) | 0900963 |
| Jul. 10, 2009 | (SE) | 0900965 |
| Jul. 10, 2009 | (SE) | 0900966 |
| Jul. 10, 2009 | (SE) | 0900968 |
| Jul. 10, 2009 | (SE) | 0900969 |
| Jul. 10, 2009 | (SE) | 0900970 |
| Jul. 10, 2009 | (SE) | 0900973 |
| Jul. 10, 2009 | (SE) | 0900974 |
| Jul. 10, 2009 | (SE) | 0900976 |
| Jul. 10, 2009 | (SE) | 0900978 |
| Jul. 10, 2009 | (SE) | 0900981 |
| Jul. 10, 2009 | (SE) | 0909972 |

(51) Int. Cl.
*A61B 17/16* (2006.01)
*A61B 17/88* (2006.01)
(Continued)

(52) U.S. Cl.
CPC ......... *A61B 17/1662* (2013.01); *A61B 17/1615* (2013.01); *A61B 17/1631* (2013.01);
(Continued)

(58) Field of Classification Search
USPC .............................. 606/79, 80, 81; 623/22.12
See application file for complete search history.

(56) References Cited

U.S. PATENT DOCUMENTS 1,308,798 A * 7/1919 Masland ........................ 606/80
1,911,764 A * 5/1933 Martin ............................ 606/80
(Continued)

FOREIGN PATENT DOCUMENTS

| DE | 3343863 | 6/1985 |
| WO | 95/01139 | 1/1995 |
| WO | WO 2008/031245 | 3/2008 |

OTHER PUBLICATIONS

International Search Report for PCT/SE2010/050823, mailed Oct. 29, 2010.

*Primary Examiner* — Christian Sevilla

(57) ABSTRACT

A surgical instrument for operating hip joint osteoarthritis in a human patient is provided. The hip joint comprises an acetabulum, being a part of the pelvic bone, and a caput femur, being the proximal part of the femoral bone. The surgical instrument is adapted to assist in the operating of the hip joint osteoarthritis from the abdominal side of the pelvic bone of said human patient.

16 Claims, 32 Drawing Sheets

Related U.S. Application Data filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009.

(51) Int. Cl.
*A61F 2/30* (2006.01)
*A61F 2/46* (2006.01)
*A61B 17/80* (2006.01)
*A61B 17/00* (2006.01)

(52) U.S. Cl.
CPC .......... *A61B17/1666* (2013.01); *A61B 17/8875* (2013.01); *A61F 2/30721* (2013.01); *A61F 2/4607* (2013.01); *A61F 2/4609* (2013.01); *A61B 17/1637* (2013.01); *A61B 17/1668* (2013.01); *A61B 17/8061* (2013.01); *A61B 2017/0034* (2013.01); *A61F 2002/30494* (2013.01); *A61F 2002/30754* (2013.01); *A61F 2002/4622* (2013.01); *A61F 2002/4628* (2013.01)

(56) References Cited

U.S. PATENT DOCUMENTS

| | | | | |
|---|---|---|---|---|
| 2,287,260 A * | | 6/1942 | Luck | 173/50 |
| 2,514,665 A * | | 7/1950 | Myller | 600/570 |
| 4,305,394 A * | | 12/1981 | Bertuch, Jr. | 606/91 |
| 4,528,980 A * | | 7/1985 | Kenna | 606/80 |
| 4,541,423 A * | | 9/1985 | Barber | 606/80 |
| 4,830,000 A * | | 5/1989 | Shutt | 606/80 |
| 4,860,735 A * | | 8/1989 | Davey et al. | 606/80 |
| 4,978,350 A * | | 12/1990 | Wagenknecht | 606/312 |
| 5,049,150 A * | | 9/1991 | Cozad | 606/80 |
| 5,120,312 A * | | 6/1992 | Wigness et al. | 604/175 |
| 5,190,548 A * | | 3/1993 | Davis | 606/80 |
| 5,269,785 A | | 12/1993 | Bonutti | |
| 5,284,483 A * | | 2/1994 | Johnson et al. | 606/86 R |
| 5,320,625 A * | | 6/1994 | Bertin | 606/91 |
| 5,350,380 A * | | 9/1994 | Goble et al. | 606/80 |
| 5,374,270 A * | | 12/1994 | McGuire et al. | 606/80 |
| 5,423,823 A * | | 6/1995 | Schmieding | 606/80 |
| 5,423,824 A * | | 6/1995 | Akerfeldt et al. | 606/80 |
| 5,437,675 A * | | 8/1995 | Wilson | 606/80 |
| 5,490,852 A * | | 2/1996 | Azer et al. | 606/79 |
| 5,490,854 A * | | 2/1996 | Fisher et al. | 606/88 |
| 5,499,984 A * | | 3/1996 | Steiner et al. | 606/80 |
| 5,584,837 A * | | 12/1996 | Petersen | 606/91 |
| D377,524 S * | | 1/1997 | Lipp | D24/144 |
| 5,645,545 A * | | 7/1997 | Bryant | 606/62 |
| 5,681,318 A * | | 10/1997 | Pennig et al. | 606/98 |
| 5,879,353 A * | | 3/1999 | Terry | 606/85 |
| 5,928,239 A * | | 7/1999 | Mirza | 606/79 |
| 5,928,241 A * | | 7/1999 | Menut et al. | 606/80 |
| 5,951,561 A * | | 9/1999 | Pepper et al. | 606/80 |
| 6,217,581 B1 * | | 4/2001 | Tolson | 606/86 R |
| 6,224,607 B1 * | | 5/2001 | Michelson | 606/96 |
| 6,358,251 B1 * | | 3/2002 | Mirza | 606/79 |
| 6,375,684 B1 * | | 4/2002 | Kriek | 623/23.39 |
| 6,395,005 B1 * | | 5/2002 | Lovell | 606/91 |
| 6,547,792 B1 * | | 4/2003 | Tsuji et al. | 606/329 |
| 6,790,210 B1 * | | 9/2004 | Cragg et al. | 606/80 |
| 7,637,910 B2 * | | 12/2009 | Schmieding et al. | 606/80 |
| 7,780,673 B2 * | | 8/2010 | Acker et al. | 606/91 |
| 7,803,159 B2 * | | 9/2010 | Perez-Cruet et al. | 606/80 |
| 7,922,720 B2 * | | 4/2011 | May et al. | 606/80 |
| 8,038,678 B2 * | | 10/2011 | Schmieding et al. | 606/80 |
| 8,048,079 B2 * | | 11/2011 | Iannarone | 606/80 |
| RE44,883 E * | | 5/2014 | Cha | 606/80 |
| RE44,896 E * | | 5/2014 | Cha | 606/80 |
| 2001/0018588 A1 * | | 8/2001 | Harder et al. | 606/80 |
| 2001/0034526 A1 * | | 10/2001 | Kuslich et al. | 606/80 |
| 2002/0032447 A1 * | | 3/2002 | Weikel et al. | 606/86 |
| 2002/0183758 A1 | | 12/2002 | Middleton et al. | |
| 2003/0130741 A1 * | | 7/2003 | McMinn | 623/23.14 |
| 2003/0158559 A1 * | | 8/2003 | Diaz | 606/91 |
| 2003/0220698 A1 * | | 11/2003 | Mears et al. | 623/22.4 |
| 2004/0024404 A1 * | | 2/2004 | Steiger et al. | 606/79 |
| 2004/0068264 A1 * | | 4/2004 | Treace | 606/86 |
| 2004/0147934 A1 * | | 7/2004 | Kiester | 606/80 |
| 2004/0167527 A1 * | | 8/2004 | Simon et al. | 606/79 |
| 2004/0171930 A1 * | | 9/2004 | Grimm et al. | 600/424 |
| 2004/0176771 A1 * | | 9/2004 | Schmieding | 606/80 |
| 2004/0199166 A1 * | | 10/2004 | Schmieding et al. | 606/79 |
| 2004/0236424 A1 * | | 11/2004 | Berez et al. | 623/14.12 |
| 2004/0247641 A1 * | | 12/2004 | Felt et al. | 424/423 |
| 2005/0085823 A1 * | | 4/2005 | Murphy | 606/91 |
| 2005/0149047 A1 * | | 7/2005 | Parry et al. | 606/99 |
| 2005/0177168 A1 * | | 8/2005 | Brunnett et al. | 606/80 |
| 2005/0240193 A1 | | 10/2005 | Layne et al. | |
| 2005/0261695 A1 * | | 11/2005 | Cragg et al. | 606/86 |
| 2005/0273107 A1 * | | 12/2005 | Stevens | 606/73 |
| 2006/0106394 A1 * | | 5/2006 | Colleran | 606/86 |
| 2006/0190078 A1 * | | 8/2006 | Fell | 623/14.12 |
| 2007/0233128 A1 * | | 10/2007 | Schmieding et al. | 606/79 |
| 2008/0039852 A1 * | | 2/2008 | Schmieding et al. | 606/88 |
| 2008/0071299 A1 * | | 3/2008 | Allinniemi et al. | 606/151 |
| 2008/0221392 A1 * | | 9/2008 | Jorgensen | 600/139 |
| 2008/0306483 A1 * | | 12/2008 | Iannarone | 606/83 |
| 2008/0312658 A1 * | | 12/2008 | Namba | 606/82 |
| 2009/0018468 A1 * | | 1/2009 | Janssens | 600/567 |
| 2009/0043344 A1 * | | 2/2009 | Schlotterback | 606/86 R |
| 2009/0076511 A1 * | | 3/2009 | Osman | 606/80 |
| 2009/0326538 A1 * | | 12/2009 | Sennett et al. | 606/80 |
| 2010/0057087 A1 * | | 3/2010 | Cha | 606/80 |
| 2010/0082033 A1 * | | 4/2010 | Germain | 606/79 |
| 2010/0082073 A1 * | | 4/2010 | Thramann | 606/86 R |
| 2010/0087828 A1 * | | 4/2010 | Krueger et al. | 606/93 |
| 2011/0238069 A1 * | | 9/2011 | Zajac et al. | 606/79 |
| 2012/0010619 A1 * | | 1/2012 | Barsoum | 606/79 |
| 2014/0074174 A1 * | | 3/2014 | Schacherer et al. | 606/286 |

* cited by examiner

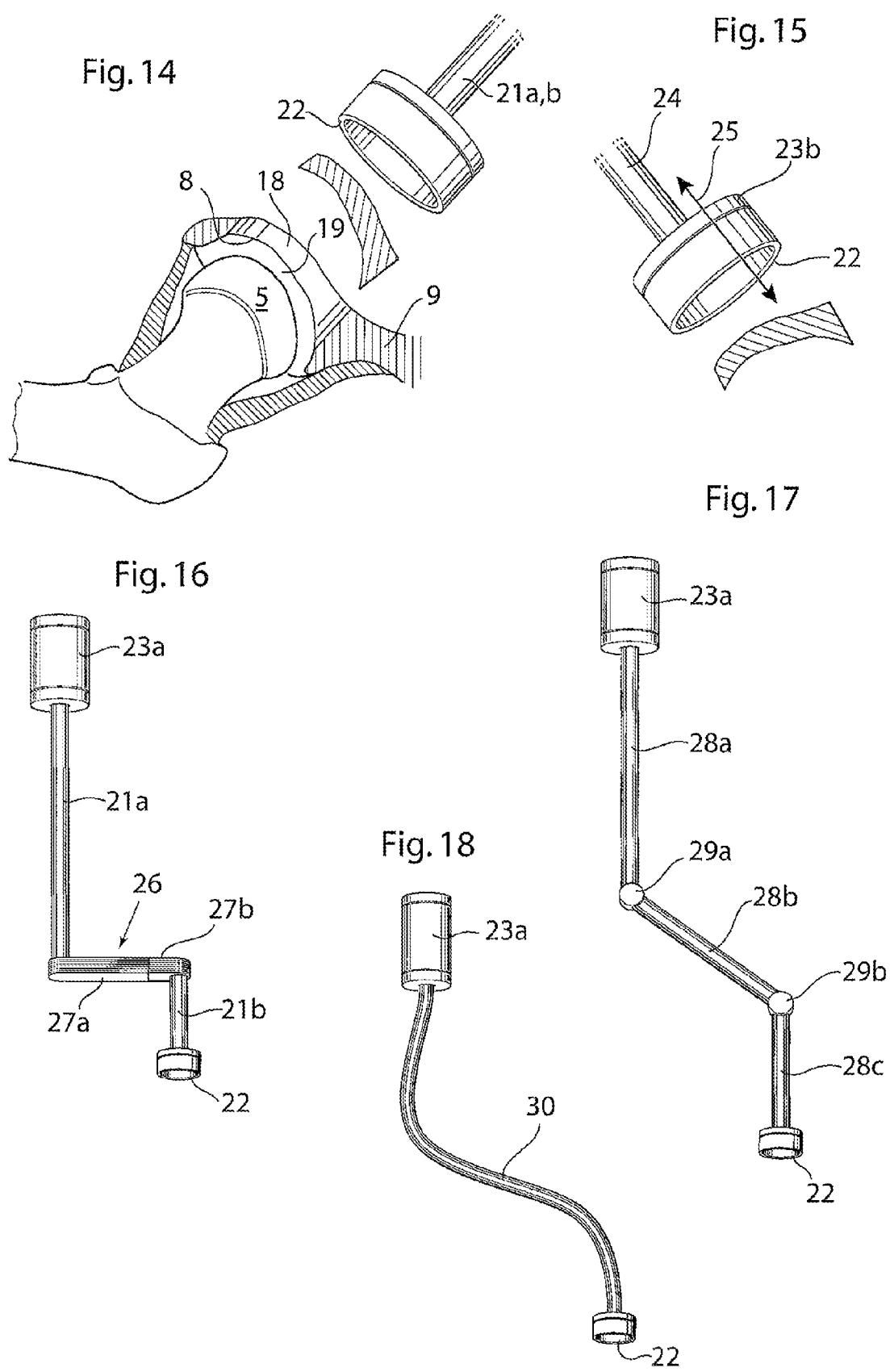

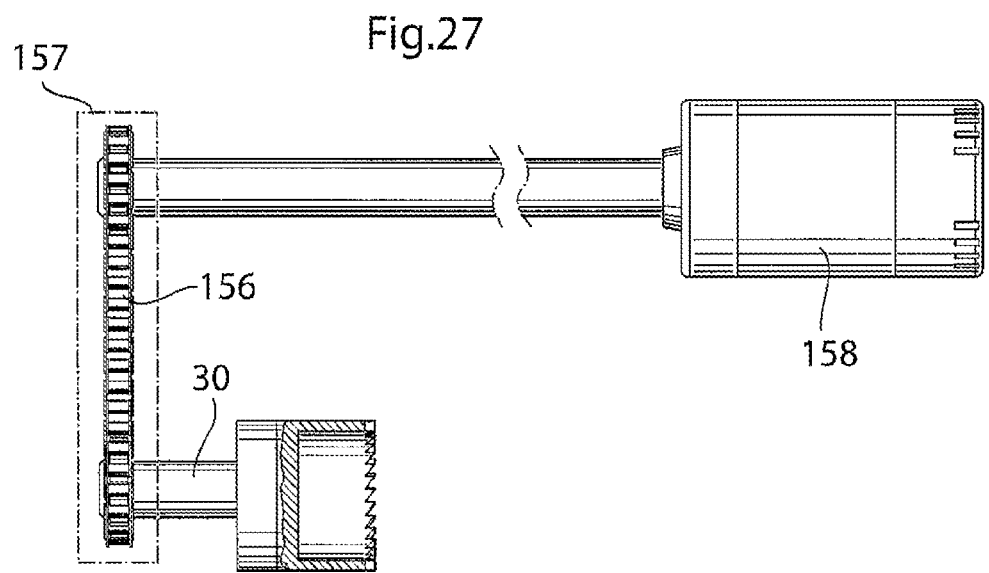
Fig.27
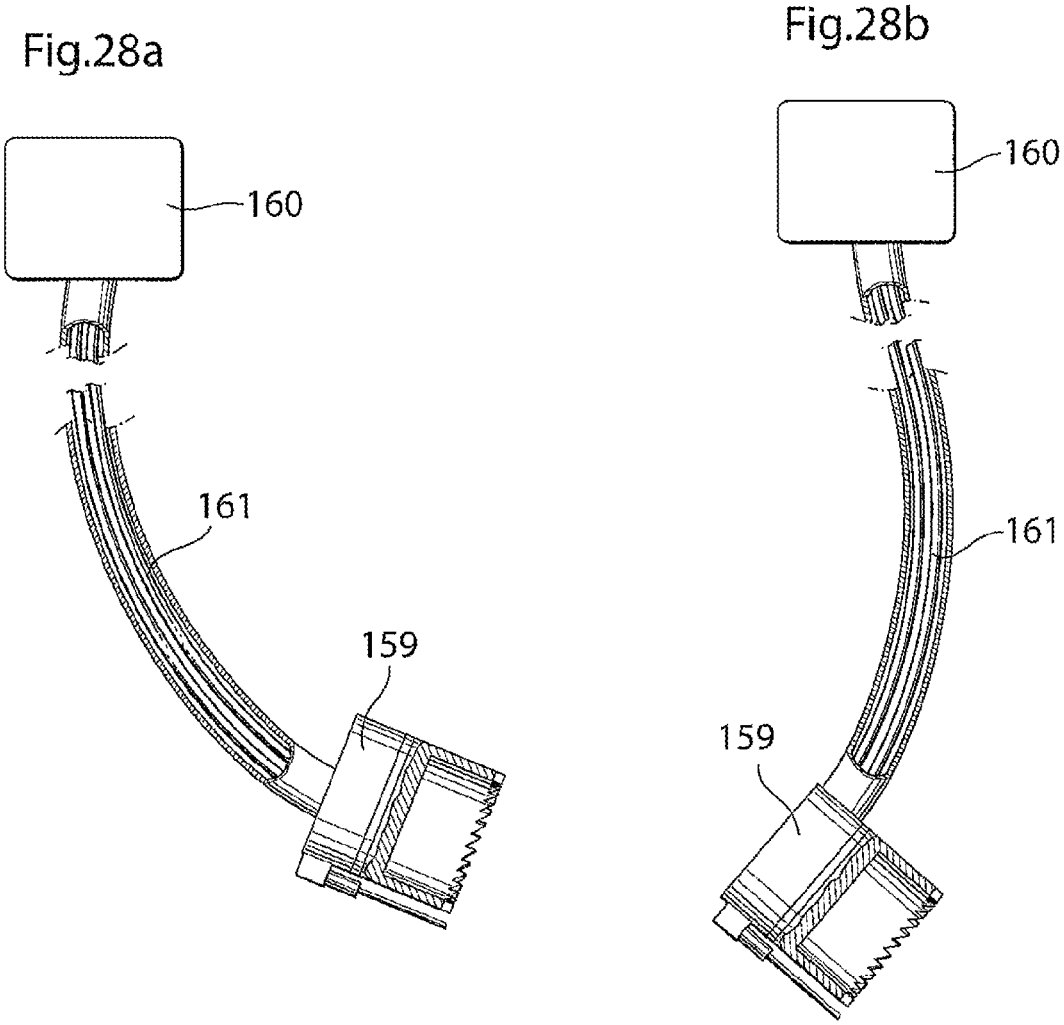
Fig.28a
Fig.28b

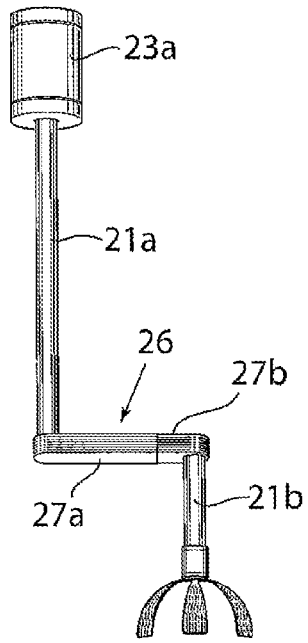
Fig.35
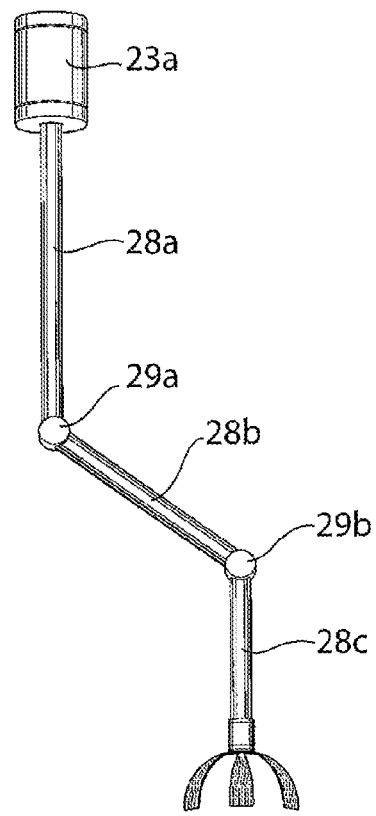
Fig.36
Fig.37
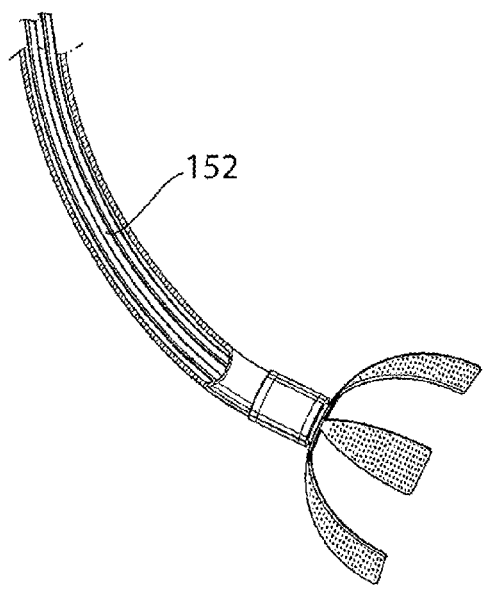
Fig.38

Fig.43
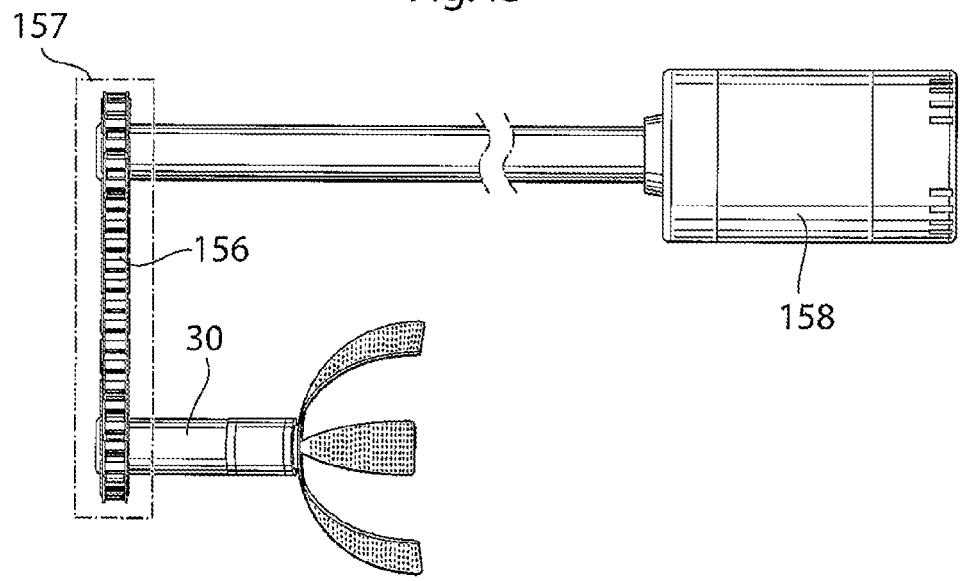
Fig.44
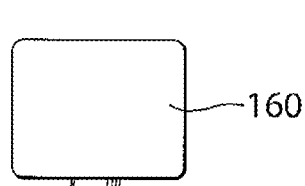
Fig.45
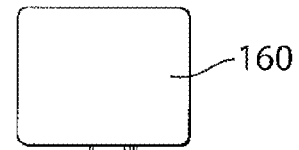
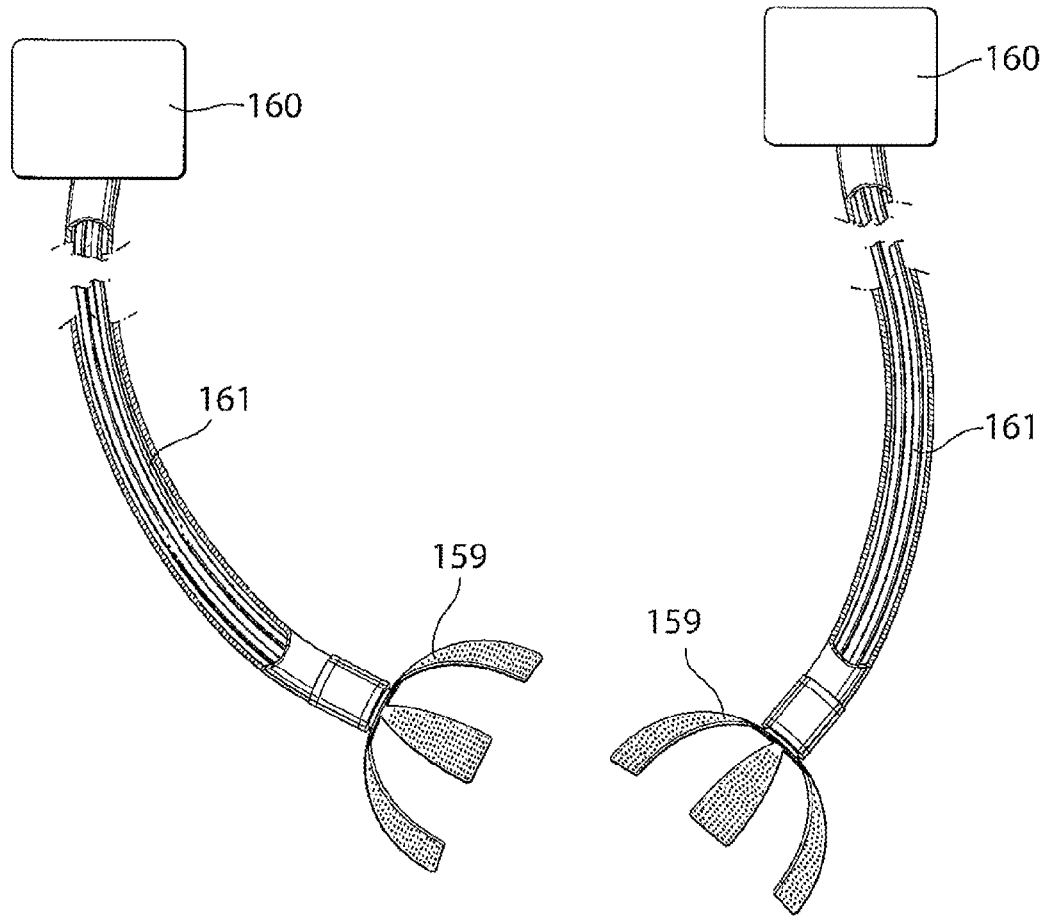

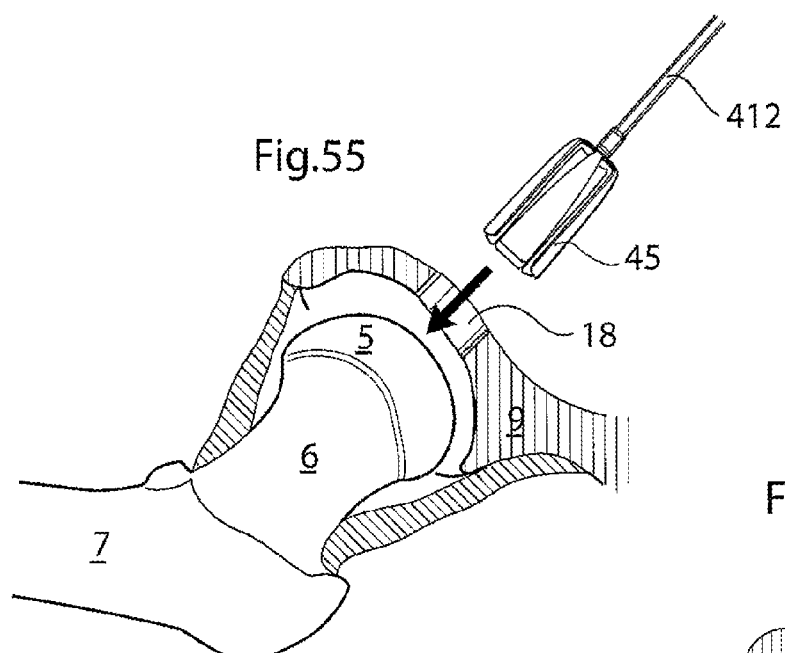
Fig.55
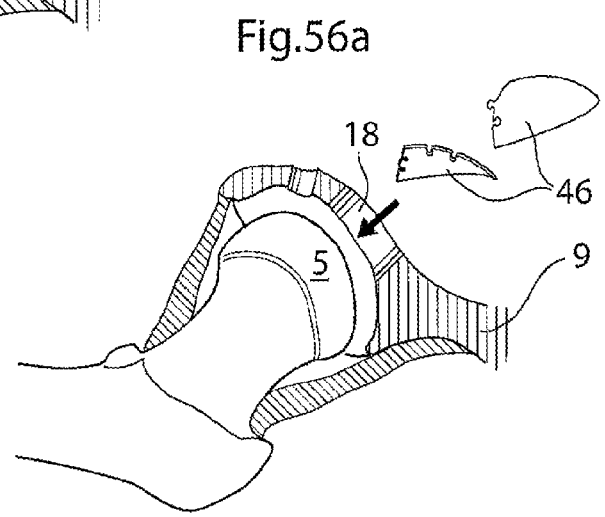
Fig.56a
Fig.56c
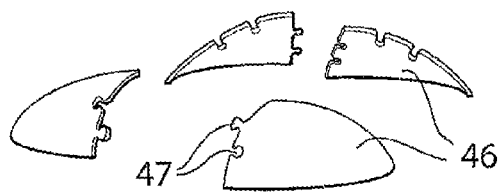
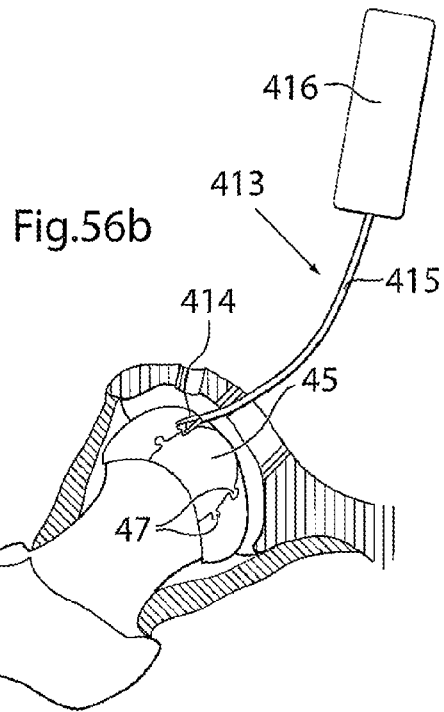
Fig.56b

Fig.64
Fig.65
Fig.66
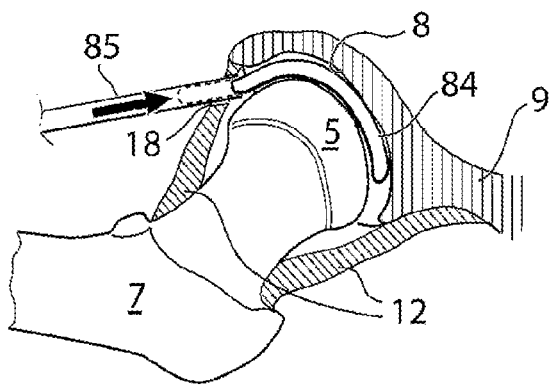
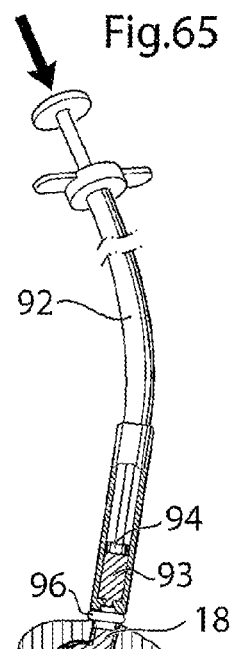
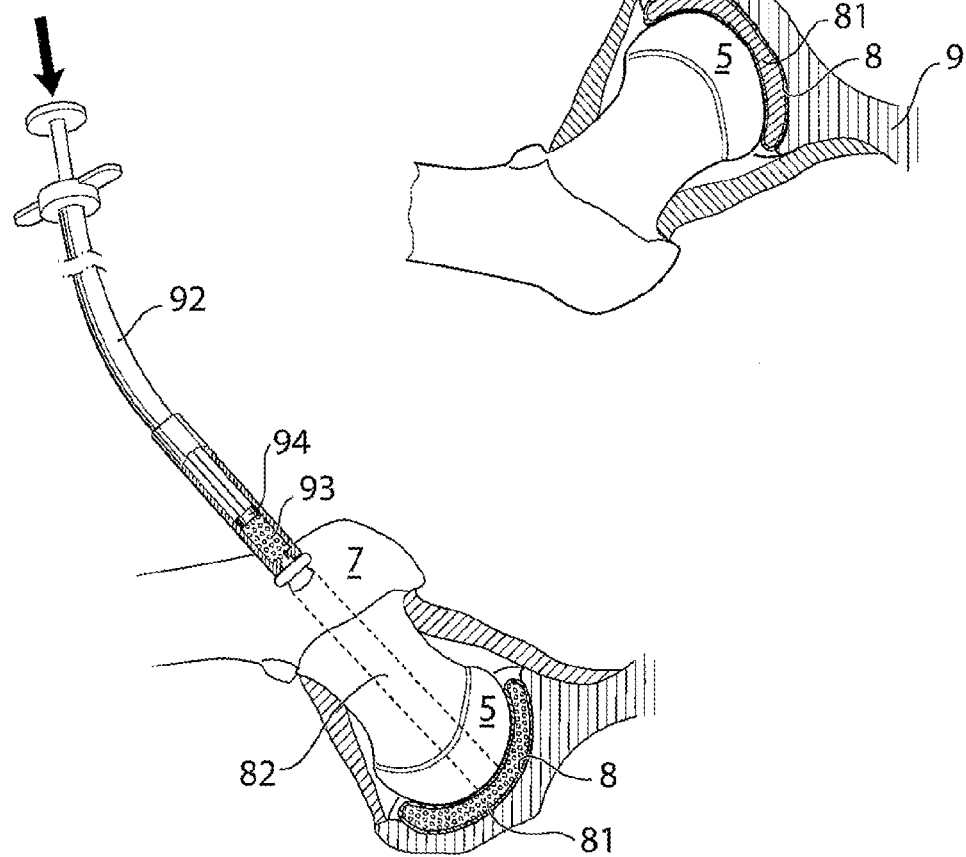

HIP JOINT INSTRUMENT AND METHOD

This application is the U.S. national phase of International Application No. PCT/SE2010/050823, filed 12 Jul. 2010, which designated the U.S. and claims the benefit of U.S. Provisional No. 61/229,755, filed 30 Jul. 2009; 61/229,738 filed 30 Jul. 2009; 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 0900974-7 filed 10 Jul. 2009; 0900976-2 filed 10 Jul. 2009 and 0900978-8 filed 10 Jul. 2009, the entire contents of each of which are hereby incorporated by reference.

FIELD OF INVENTION

The present invention relates generally to a surgical instrument for use in treating of hip osteoarthritis in a human patient.

BACKGROUND

Hip Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip Osteoarthritis is estimated to affect 80% of all people over 65 years of age, in more or less serious forms.

The present treatments for hip osteoarthritis comprises NSAID drugs, local injections of Hyaluronic acid or Glucocorticoid to help lubricating the hip joint, and replacing parts of the hip joint with a prosthesis through hip joint surgery.

Replacing parts of the hip joint is one of the most common surgeries to date performed at hundreds of thousand of patients in the world every year. The most common method comprises placing a metal prosthesis in Femur and a plastic bowl in Acetabulum. This operation is done through a lateral incision in the hip and upper thigh, through Fascia Lata and the lateral muscles of the thigh. To get access to the joint, the supporting Fibrous Capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The surgery typically requires one week of hospitalization due to the increased risk of infection. The recovery process is on average about 6 weeks, but even after that the patient should not perform any physical activates that places large strain on the joint.

SUMMARY

A first object is to provide a surgical instrument for operating hip joint osteoarthritis in a human patient. The hip joint comprises an acetabulum being a part of the pelvic bone, and a caput femur being the proximal part of the femoral bone. The surgical instrument comprises an abdominal portion insertable through an incision in the skin in the abdominal region and adapted to be placed between the incision in the abdominal region and the pelvic bone when the instrument is in use, and a pelvic portion connected to the abdominal portion, being partially insertable through a hole in the pelvic bone from the abdominal side of the pelvic bone, when the instrument is in use, wherein a portion of the pelvic portion is adapted to operate at least partially in a surgically created hole in the pelvic bone.

According to one embodiment the surgical instrument is further adapted to operate through a hole in the pelvic bone of said human patient. For this purpose the instrument could be adapted to be bent, by means of: a fixed angle, an adjustable angle, a parallel displaced part or section, at least one gear wheel or at least one universal joint. It is furthermore conceivable that the surgical instrument is adapted to be curved in such a way that it is adapted to be introduced through the skin and further into the hole in the pelvic bone from the abdominal side thereof and further into the hip joint.

According to one embodiment the length of the surgical instrument is adapted to reach the hip joint from the abdominal side of said pelvic bone. The surgical instrument could further comprise a gripping end and an end reaching the hip joint, in which case the distance between said gripping end and a part of said surgical instrument adapted to be bent could be adapted for operating in a hip joint from the abdominal side of said pelvic bone. It is also conceivable that the length between said gripping end and said end reaching the hip joint is adapted for operating in a hip joint from the abdominal side of said pelvic bone.

According to another embodiment the surgical instrument is a special laparoscopic instrument introduced into the abdomen and further down to the pelvic bone on the opposite side of the acetabulum and introduced into the hip joint. The instrument could further comprise a gripping end, placed outside the abdominal wall when in use, and a hip joint end adapted to be placed in an area of the hip joint. The length of the instrument could be adapted to reach from the gripping end and into the hip joint via a surgically created hole in the pelvic bone and wherein the longitudinal extension of the instrument comprises at least one bend, for the instrument to reach, when used as a special laparoscopic instrument to operate the hip joint, from the gripping end into the abdomen and further down to the pelvic bone on the opposite side of the acetabulum and be introduced into the hip joint through the surgically created hole in the pelvic bone.

According to yet another embodiment the surgical instrument is a special pelvic instrument adapted to be introduced into the pelvic region and further to the pelvic bone on the opposite side of the acetabulum, and introduced into the hip joint via a surgically created hole in the pelvic bone. The instrument could further comprise a gripping end, placed outside the skin above the pelvic region when in use, and a hip joint end adapted to be placed in an area of the hip joint, wherein the length of said instrument is adapted to reach from the gripping end and into the hip joint, and wherein the longitudinal extension of said instrument comprises at least one bend, for the instrument to reach, when used as special pelvic instrument to operate the hip joint, from the gripping end into the pelvic region and further down to the pelvic bone on the opposite side of the acetabulum, and introduced into the hip joint through the surgically created hole in the pelvic bone.

According to yet another embodiment, the surgical instrument could be adapted to be a special retroperitoneal instrument introduced into the body just above the inguinal region following the pelvic bone down to the opposite side of the acetabulum and thereafter introduced into the hip joint via a surgically created hole in the pelvic bone. The instrument could comprise a gripping end, placed outside the skin above the pelvic region when in use, and a hip joint end adapted to be placed in an area of the hip joint. The length of the instrument is adapted to reach from the gripping end and into the hip joint and the longitudinal extension of said instrument comprises at least one bend, for the instrument to reach, when used as special retroperitoneal instrument to operate the hip joint, from the gripping end following the pelvic bone and further down to the pelvic bone on the opposite side of the acetabulum and introduced into the hip joint through the surgically created hole in the pelvic bone.

The surgical instrument according to any of the embodiments could comprise at least one holding part and a mechanical element adapted to be fitted to the at least one holding part of the instrument. The surgical instrument could be adapted to perform a function during an operation of the hip joint. The mechanical element could in turn be adapted to be part of an instrument adapted to be used for at least one of the following functions; drilling, reaming, cooling, heating, flushing, introducing a fluid, sucking, inserting at least one part, connecting at least one part, fixating at least one part, inserting a mould, filling a mould, injecting, lubricating, viewing, optically displaying, placing screws, placing adhesive, placing bone cement.

The surgical instrument could have a distance between the gripping end and the bend that is at least 10 cm, it is furthermore conceivable that the distance between the gripping end and the bend is at least 20 cm. It is furthermore conceivable that the distance between the gripping end and the bend is at least 30 cm. It is furthermore conceivable that the distance between the gripping end and the bend is at least 40 cm. It is furthermore conceivable that the distance between said gripping end and said bend is at least 50 cm.

According to one embodiment the surgical instrument comprises a bend, and wherein the bend is bent with an angle of at least 10 degrees, the bend is bent with an angle of at least 20 degrees or the bend is bent with an angle of at least 30 degrees, or the bend is bent with an angle of at least 40 degrees, or the bend is bent with an angle of at least 50 degrees, or the bend is bent with an angle of at least 60 degrees.

According to one embodiment the of the surgical instrument, the distance between the bend and the hip joint end of the instrument is at least 2 cm, according to another embodiment the distance between the bend and the hip joint end of the instrument is at least 4 cm, according to yet another embodiment the distance between the bend and the hip joint end of the instrument is at least 6 cm, according to yet another embodiment the distance between the bend and the hip joint end of the instrument is at least 8 cm, according to yet another embodiment the distance between the bend and the hip joint end of the instrument is at least 10 cm, according to yet another embodiment the distance between the bend and the hip joint end of the instrument is at least 12 cm, according to yet another embodiment the distance between the bend and the hip joint end of the instrument is at least 14 cm,

APPLICATIONS OF THE INSTRUMENT

The surgical instrument could be adapted for a number of applications. According to a first embodiment the surgical instrument is adapted to create a through-going hole in the pelvic bone placed in the acetabulum area from the abdominal side of the pelvic bone of said human patient. According to this embodiment the surgical instrument could comprise: a driving member, a bone contacting organ in connection with said driving member, and an operating device adapted to operate said driving member.

According to one embodiment the surgical instrument is adapted to ream the acetabulum and or the caput femur of said human patient. According to this embodiment the surgical instrument could be adapted to be expandable, thus allowing the surgical instrument to be inserted through a hole in the pelvic bone smaller than the area possible to ream using said surgical instrument. The surgical instrument adapted to ream could comprise: a driving member, a bone contacting organ in connection with said driving member, and an operating device, adapted to operate said driving member. The bone contacting organ could comprise at least one of the materials: titanium, ceramics or stainless steel. The operating device could be: electrically operated hydraulically operated and comprise at least one camera and/or at least one light source.

According to one embodiment the surgical instrument is adapted to cool an area of the hip joint or the pelvic bone. The cooling could be provided using a cooling fluid and could be provided before, during or after the creation of a hole in the pelvic bone. It is also conceivable that the cooling is provided before, during or after a reaming operation.

According to one embodiment the surgical instrument is adapted to provide a fluid to an area of the pelvic bone or the hip joint. The fluid could be adapted to clean or sterilize an area of the pelvic bone or an area of the hip joint.

According to one embodiment the surgical instrument is adapted to provide suction to an area of the pelvic bone or the hip joint. The surgical instrument adapted to provide suction could further be adapted to transport body fluids, parts of bone, cartilage or a fluid provided during the hip joint surgery.

According to one embodiment the surgical instrument is adapted to introduce prosthesis or at least one prosthetic part into the hip joint. The prosthesis or prosthetic part could be acetabulum prosthesis or a part of acetabulum prosthesis or caput femur prosthesis or a part of caput femur prosthesis.

According to one embodiment the surgical instrument is adapted to connect at least two prosthetic parts to each other after insertion into the hip joint. The at least two prosthetic parts could comprises at least two artificial caput femur surface parts or at least two artificial acetabulum surface parts. The fixation could be done using at least one of: screws, form fitting, welding, adhesive, sprint, band, or other mechanical connecting members.

According to one embodiment the surgical instrument is adapted to fixate a hip joint surface, or a part of a hip joint surface, to the pelvic bone or the femur bone. The fixation could be done using at least one of: screws, form fitting, welding, adhesive, sprint, band, or other mechanical connecting members.

According to one embodiment the surgical instrument is adapted to introduce a mould or at least one sealing member into the hip joint. The mould or sealing member could be adapted to be resorbable by the human body or melt after having served its purpose as mould. According to this embodiment the surgical instrument could comprise gripping means for gripping said mould or sealing member.

According to one embodiment the surgical instrument is adapted to inject a fluid, adapted to harden to provide an artificial hip joint surface in the hip joint, into a mould or a sealed area of the hip joint. According to this embodiment the surgical instrument could comprise at least one container, a fluid injecting member in connection with said mould, and a fluid driving member in fluid connection with said fluid injecting member and said at least one container.

According to one embodiment the surgical instrument comprises at least two containers adapted to hold two different fluids, and a mixing unit adapted to mix said fluids contained in said at least two containers.

According to one embodiment the surgical instrument is adapted to introduce adhesive or bone cement into the hip joint. According to this embodiment the surgical instrument could comprise: at least one container, a fluid injecting member, and a fluid driving member in fluid connection with said fluid injecting member and said at least one container. According to one embodiment the surgical instrument comprises at least two containers adapted to hold two different fluids, and a mixing unit adapted to mix said fluids contained in said at least two containers.

According to one embodiment the surgical instrument is adapted to place or fixate fixating elements to the pelvic bone or a prosthetic part in the pelvic region. The fixating elements could comprise: at least one screw, at least one plate and/or at least one nut.

According to one embodiment the surgical instrument comprises at least one camera, at least one light source or an x-ray tube or x-ray detector.

According to one embodiment the surgical instrument is adapted to inject a lubricating fluid into the hip joint, in which case the surgical instrument could comprise: at least one container, a fluid injecting member, and a fluid driving member in fluid connection with said fluid injecting member and said at least one container. The lubricating fluid is preferably a biocompatible lubricating fluid, such as hyaluronic acid.

Please note that any embodiment or part of embodiment, feature, method, associated system, part of system described herein may be combined in any way.

BRIEF DESCRIPTION OF THE DRAWINGS

The embodiments are now described, by way of example, with reference to the accompanying drawings, in which:

FIG. 14 shows an instrument adapted to create a hole in the pelvic bone,
FIG. 15 shows an instrument adapted to create a hole in the pelvic bone in further detail,
FIG. 16 shows an instrument adapted to create a hole in the pelvic bone comprising a parallel displaced part or section,
FIG. 17 adapted to create a hole in the pelvic bone comprising two joints,
FIG. 18 shows an instrument adapted to create a hole in the pelvic bone comprising a flexible part or section,
FIG. 27 shows an instrument adapted to create a hole in the pelvic bone comprising a chain according to another embodiment,
FIG. 28a shows an instrument adapted to create a hole in the pelvic according to another embodiment,
FIG. 28b shows an instrument adapted to create a hole in the pelvic according to another embodiment,
FIG. 35 shows an instrument adapted to ream, comprising a parallel displaced part or section,
FIG. 36 shows an instrument adapted to ream comprising two joints,
FIG. 37 shows an instrument adapted to ream comprising a flexible part or section,
FIG. 38 shows an instrument adapted to ream, in further detail,
FIG. 43 shows an instrument adapted to ream, comprising a chain, according to another embodiment,
FIG. 44 shows an instrument adapted to ream, according to another embodiment,
FIG. 45 shows an instrument adapted to ream, according to another embodiment,
FIG. 55 shows the insertion of prosthesis, through a hole in the pelvic bone,
FIG. 56a shows the insertion of prosthetic parts, through a hole in the pelvic bone,
FIG. 56b shows the connecting of prosthetic parts, through a hole in the pelvic bone,
FIG. 56c shows prosthetic parts,
FIG. 64 shows the insertion of a mould or a sealing member, through the hip joint capsule,
FIG. 65 shows the injection of fluid into a mould, through the hip joint,
FIG. 66 shows the injection of fluid into a mould, through the femoral bone.

DETAILED DESCRIPTION

Figure 1:
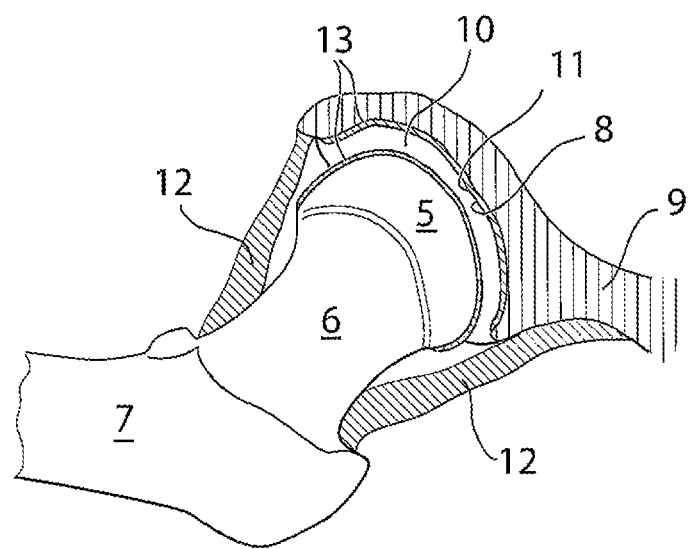
FIG. 1 shows a hip joint in section.

In the following a detailed description of embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

Please note that any embodiment or part of embodiment as well as any method or part of method could be combined in any way. All examples herein should be seen as part of the general description and therefor possible to combine in any way in general terms.

FIG. 1 shows the hip joint of a human patient in section. The hip joint comprises a caput femur 5 placed at the very top of collum femur 6 which is the top part of the femur bone 7. The caput femur is in connection with the acetabulum 8 which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down sometimes due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Figure 2:
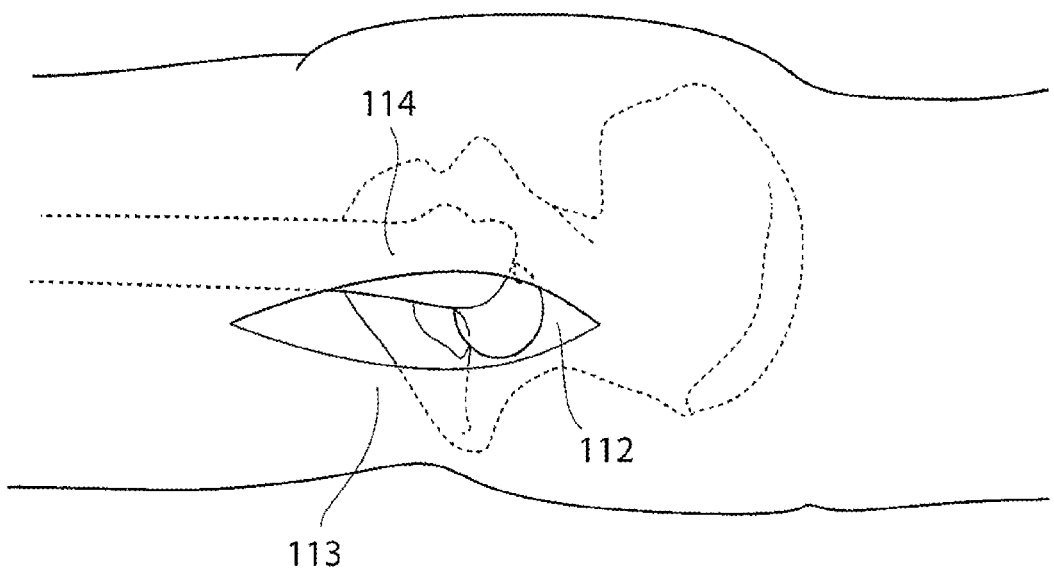
FIG. 2 shows a lateral view of a conventional hip joint surgery.

FIG. 2 shows a lateral view of a conventional hip joint surgery where an incision 112 is made in the thigh 113 enabling the surgeon to reach the femur bone 7 on which the caput femur 5 is located. In a conventional hip joint surgery the hip joint is accessed through the hip joint capsule.

Figure 3:
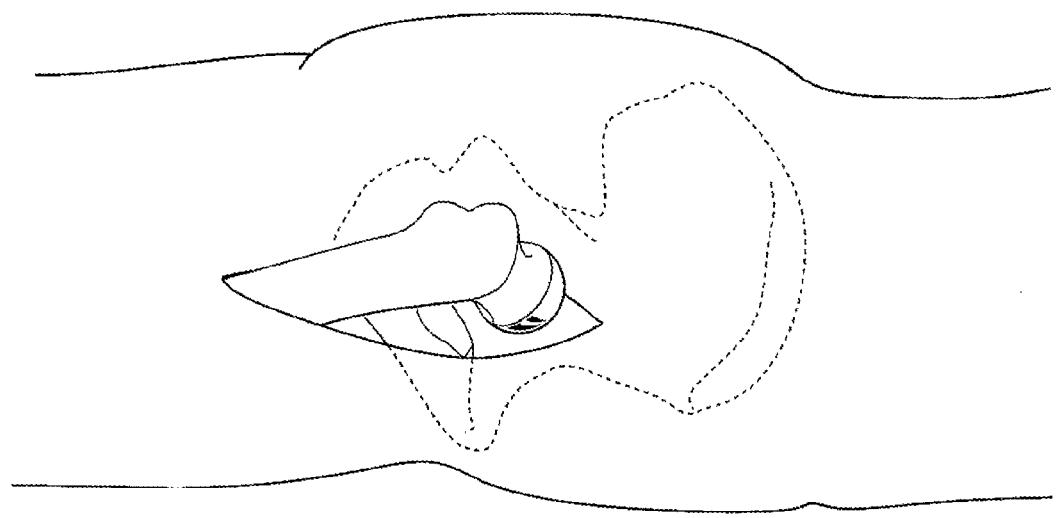
FIG. 3 shows an artificial caput femur being used in conventional surgery.

FIG. 3 shows the placing of an artificial caput femur surface 45 on the caput femur 5 in conventional surgery.

Figure 4:
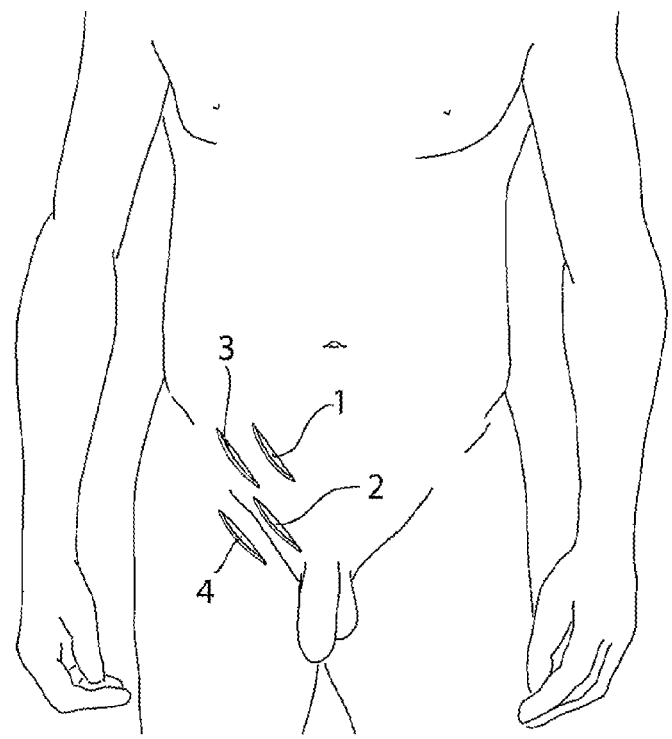
FIG. 4 shows a frontal view of the body of a human patient.

FIG. 4 shows a frontal view of the body of a human patient. A surgical method of operating the hip joint from the opposite side from acetabulum, is according to a first embodiment performed starting with an incision 1 in the abdominal wall of the human patient. The incision 1 passes through the abdominal wall sometimes including the rectus abdominis and including peritoneum in to the abdomen of the human patent. In a second embodiment the incision 2 is conducted through the skin and into the pelvic area, below peritoneum. According to a third embodiment the incision 3 is performed just between Illium and the surrounding tissue, an incision 3 which could enable the pelvic bone to be dissected with very little penetration of fascia and muscular tissue. According to a fourth embodiment the incision 4 is made in the inguinal region or slightly above. In all of the four embodiments the tissue surrounding the pelvic bone 9 in the area opposite to acetabulum is removed or penetrated which enables the surgeon to reach the pelvic bone 9.

Figure 5:
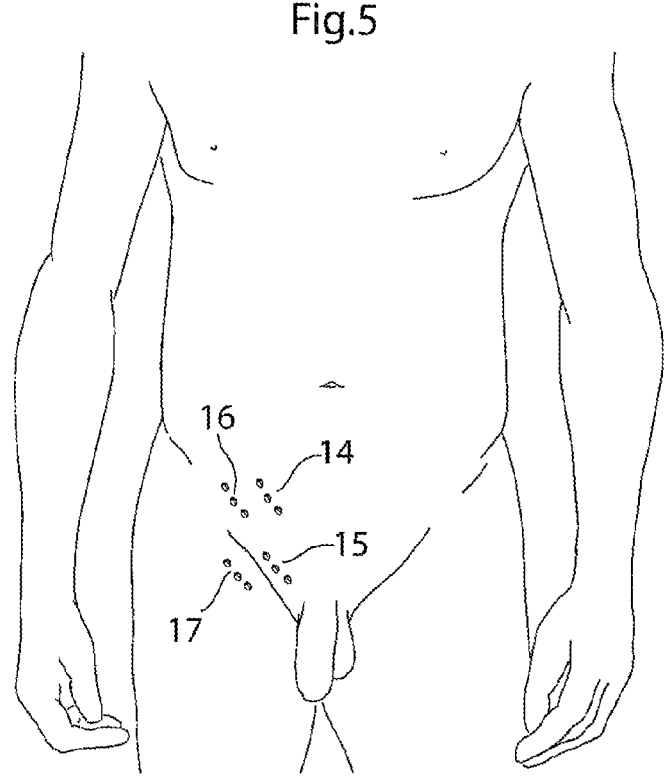
FIG. 5 shows a frontal view of the body of a human patient.

FIG. 5 shows a frontal view of the body of a human patient. A laparoscopic method of operating the hip joint, from the opposite side from acetabulum, is according to a first embodiment performed starting with making small incisions 14 in the abdominal wall of the human patient. The small incisions enable the surgeon to insert laparoscopic trocars into the abdomen of the human patient. According to the first embodiment the incisions 14 passes through the abdominal wall including the peritoneum in to the abdomen of the human patent. According to a second embodiment the small incisions 15 is conducted through the skin and in to the pelvic area, below peritoneum. According to a third embodiment the small incisions 16 is performed just between Illium and the surrounding tissue, an incision 16 which could enable the pelvic bone to be dissected with very little penetration of fascia and muscular tissue. According to a fourth embodiment the incision 17 is made in the inguinal channel. In all of the four embodiments the tissue surrounding the pelvic bone 9 in the area opposite to acetabulum 8 is removed or penetrated which enables the surgeon to reach the pelvic bone 9.

After the incision is made the surgical instruments according to any on the embodiments below can enter the human buoy and be used to assist the surgeon in the operation of the hip joint osteoarthritis.

Figure 6:
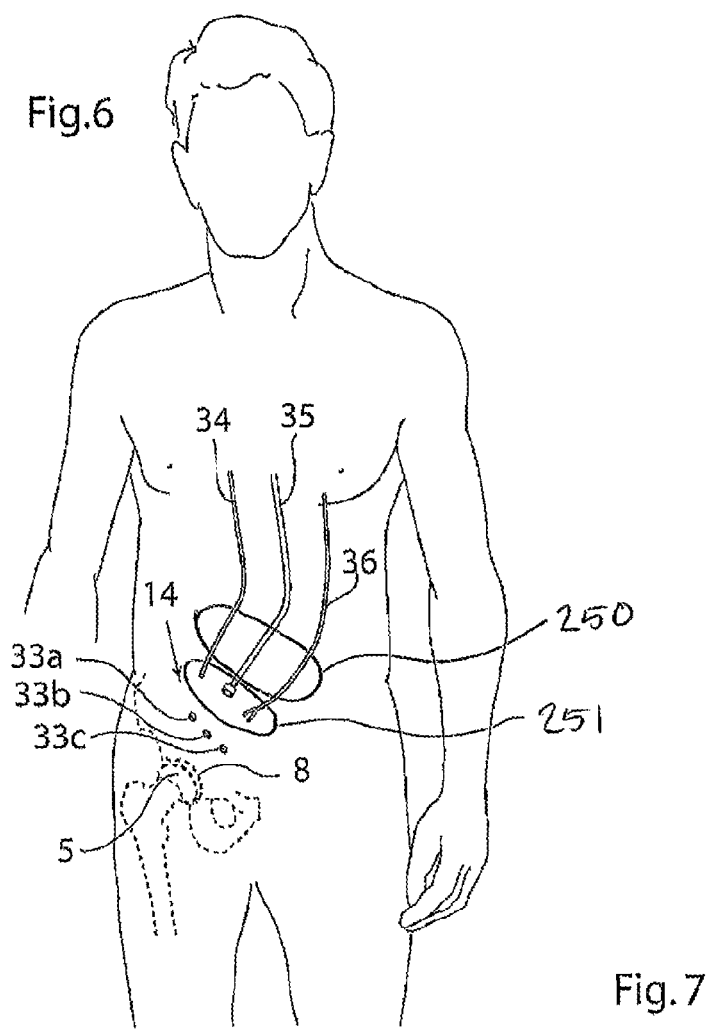
FIG. 6 shows a frontal view of the body of a human patient.

FIG. 6 shows a frontal view of the body of a human patient, illustrating the instruments 34, 35, 36 assisting in the method of operating the hip joint from the opposite side from acetabulum 8, the hip joint comprising the acetabulum 8 and the caput femur 5. The small incisions 14 in the abdominal wall of the human patient allows the insertion of laparoscopic trocars 33a,b,c into the body of the patients. Whereafter one or more camera 34, a surgical instrument 35 adapted to create a hole in the pelvic bone 9, or instruments 36 for introducing, placing, connecting, attaching, creating or filling prosthesis or prosthetic parts, can be inserted into said body through said laparoscopic trocars 33a,b,c. many different placements of the trocars is possible. The portions of the instruments adapted to be placed in the abdominal area are the abdominal portions 250, and the portions adapted to at least partially be placed inside of the pelvic bone is the pelvic portions 251 throughout this application.

Figure 7:
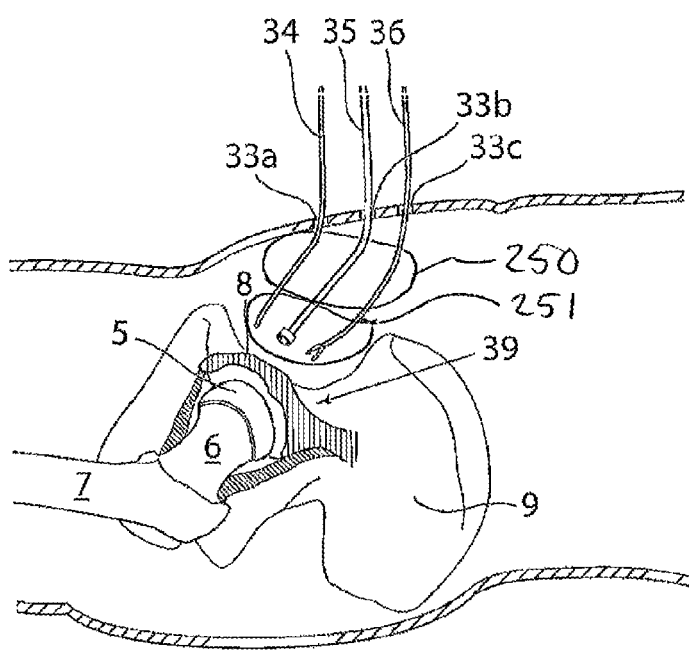
FIG. 7 shows a lateral view of the body of a human patient in section.

FIG. 7 shows a lateral view of the body of a human patient, with the hip joint shown in section in further detail. The hip joint comprises a caput femur 5 placed at the very top of collum femur 6 which is the top part of the femur bone 7. The caput femur is in connection with the acetabulum 8 which is a bowl shaped part of the pelvic bone 9. Laparoscopic trocars 33a,b,c is being used to reach the hip joint 39 with one or more camera 34, a surgical instrument adapted to create a hole in the pelvic bone 35, or instruments 36 for introducing, placing, connecting, attaching, creating or filling prosthesis or prosthetic parts. The portions of the instruments adapted to be placed in the abdominal area are the abdominal portions 250, and the portions adapted to at least partially be placed inside of the pelvic bone is the pelvic portions 251 throughout this application.

Figure 8A:
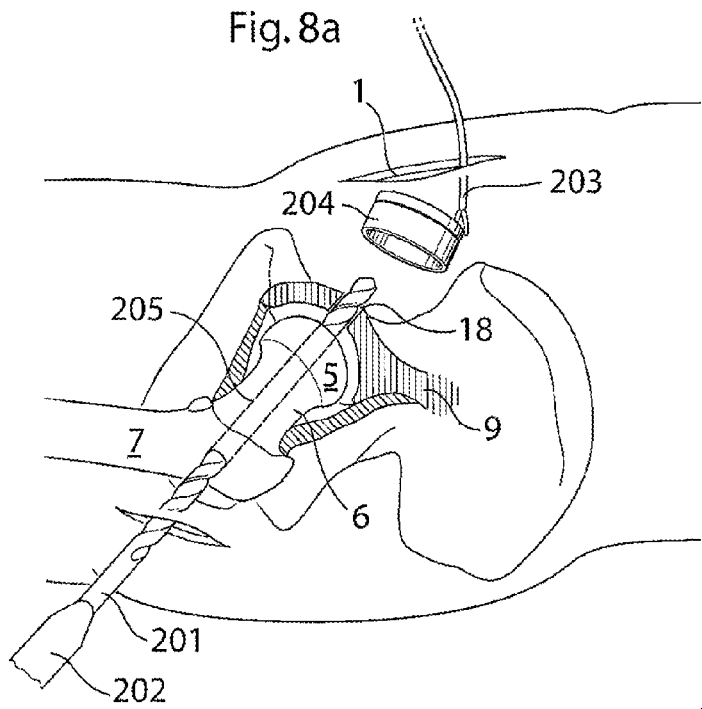
FIG. 8a shows the creation of a hole through the collum femur, in a length axis thereof.

FIG. 8a shows a human patient in section when an incision 1 is made in the abdominal wall of the human patient, and a second incision 200 in made in the lateral part of the left thigh. A drilling member 201 has been introduced through the incision 200 in the thigh, penetrating the fascia lata, and reaching the femoral bone 7. After the drilling member 201 has made contact with the femoral bone 7, a drilling process is started which creates a hole 205 in the cortical bone of the femoral bone 7 and into the cancellous bone of the femoral bone 7, the hole 205 then propagates along a length axis of the collum femur 6 and eventually reaches the caput femur 5, from the inside thereof. The caput femur 5 is penetrated from the inside and the drilling member 201 continues to the acetabulum 8 which is a bowled shaped part of the pelvic bone 9. The drilling member 201 penetrates the pelvic bone 9 and continues into the abdominal area of the human patient. The drilling member 201 is then retracted from the hole 205 which leaves a hole 201 reaching from the lateral side of the thigh, to the area of the hip joint. The drilling member 201 is powered by an operating device 202 which could be an electrically, hydraulically or pneumatically powered operating device 202.

After the hole 205 has been created along a length axis of the collum femur 6, a force transferring member 206 is inserted through the hole 205. The force transferring member 206 could be a tubular or solid shaft, or a flexible member such as a wire.

Figure 8B:
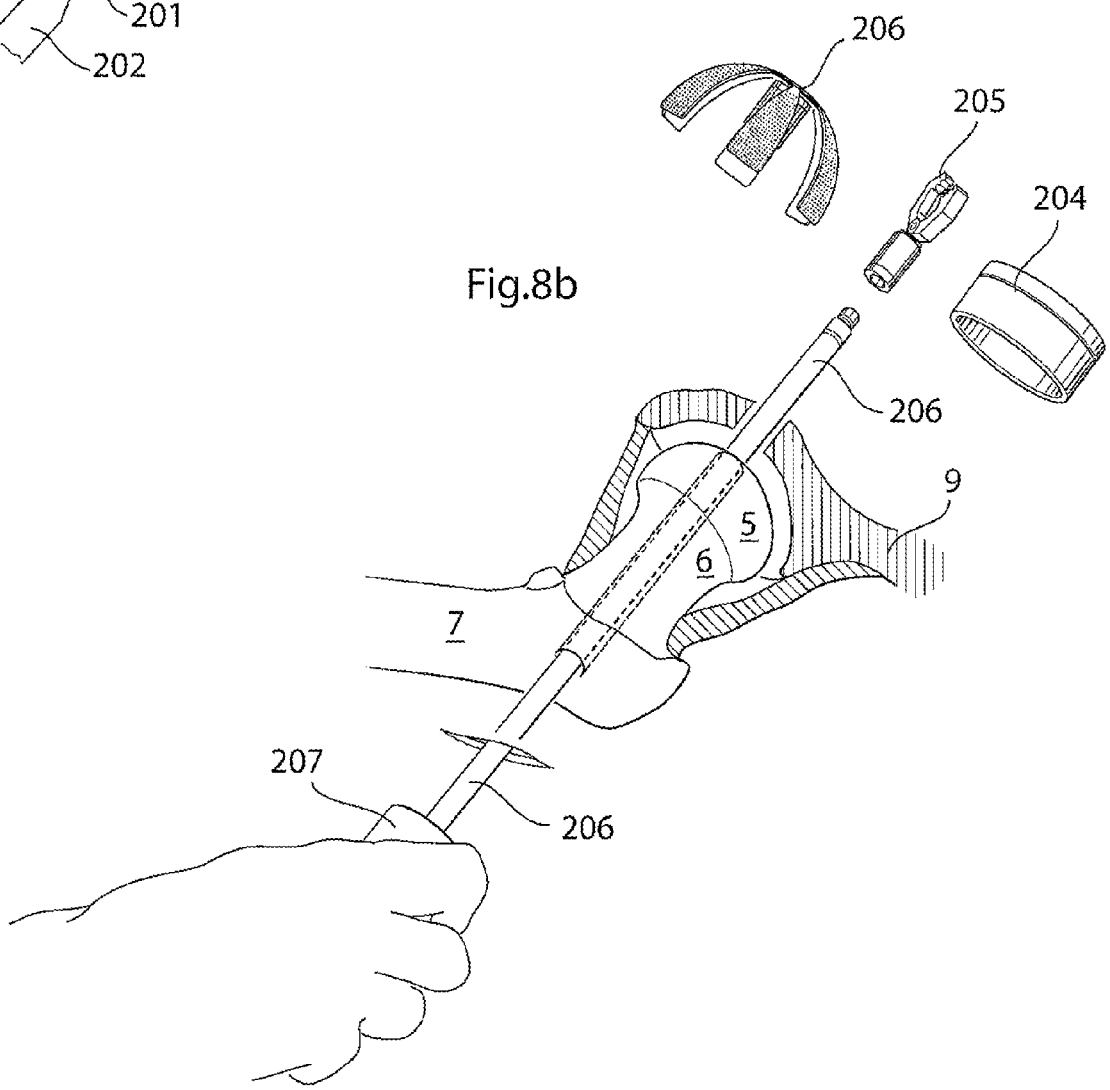
FIG. 8b shows mechanical instruments adapted to be placed on an elongated member placed in a hole in collum femur.

FIG. 8b shows the hip joint in section when a force transferring member 206 has been inserted through the hole 205. The force transferring member 206 comprises a tool fixating member 218 positioned on the end of the force transferring member 206. The tool fixating member 218 could comprise a screw-thread or a bayonet joint which could be activated to fixate a tool 224,225,226 to the force transferring member 206, by the turning of said force transferring member by means of manual manipulation or an operating device 207. FIG. 5 further shows a tool for creating a hole 224 in the pelvic bone 9, a tool 225 for manipulating an implantable device such as a prosthesis or a prosthetic part, and a tool 226 for reaming the acetabulum 8 and/or the caput femur 5. The tools comprise a fixating member 219 which acts together with the tool fixating member 218 on the force transferring member 206 to fixate the tool 224,225,226 to the force transferring member 206. The tools 224,225,226 is inserted through the incision in the abdominal region, as shown in FIG. 4. where a tool 224 for creating a hole in the pelvic bone 9 is inserted through an incision 1 in the abdominal region of the human patient using a tool introducing member 203. The force transferring member 206 according to any of the embodiments could be used as a positioning shaft, for positioning, centering and guiding a tool or a medical device, such as a prosthetic part.

Figure 9A:
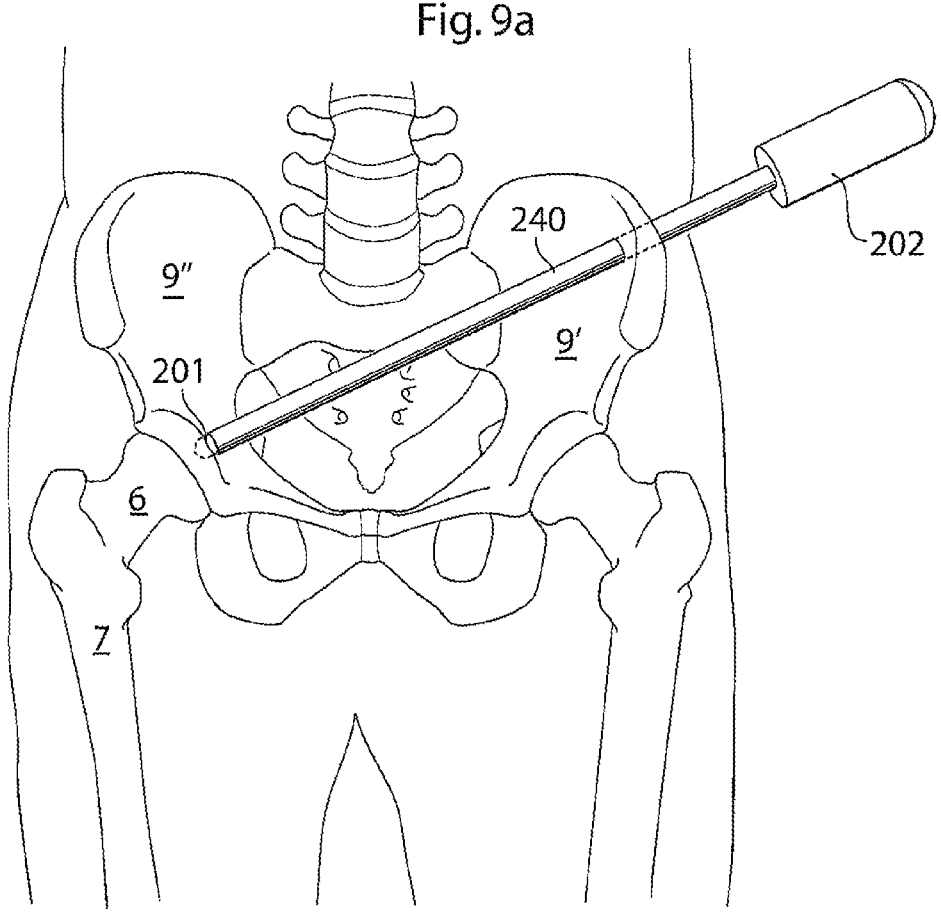
FIG. 9a shows the placement of an elongated member through the pelvic bone.

FIG. 9a shows an embodiment in which a hole is created in two different parts of the pelvic bone 9. A drilling member 201 is first brought to the left part of the pelvic bone 9' for creating a hole in the left part of the pelvic bone 9. The drilling member thereafter continues through the abdominal and/or pelvic region and reaches the right part of the pelvic bone 9" where a second hole is created reaching into the hip joint. The drilling member 201 is powered by an operation device 202, which could be a powered operation device, such as an electrical, hydraulic or pneumatic motor. According to another embodiment the drilling member 201 is manually operated. The drilling member further comprises a protective sleeve 240 adapted to protect the organs and tissue of the body from the drilling member 201 when advancing the drilling member through the abdominal and/or the pelvic region. The creation of two holes enables a very stable position of an elongated member which could be placed through the two holes for delivering an action to the hip joint or its surroundings.

Figure 9B:
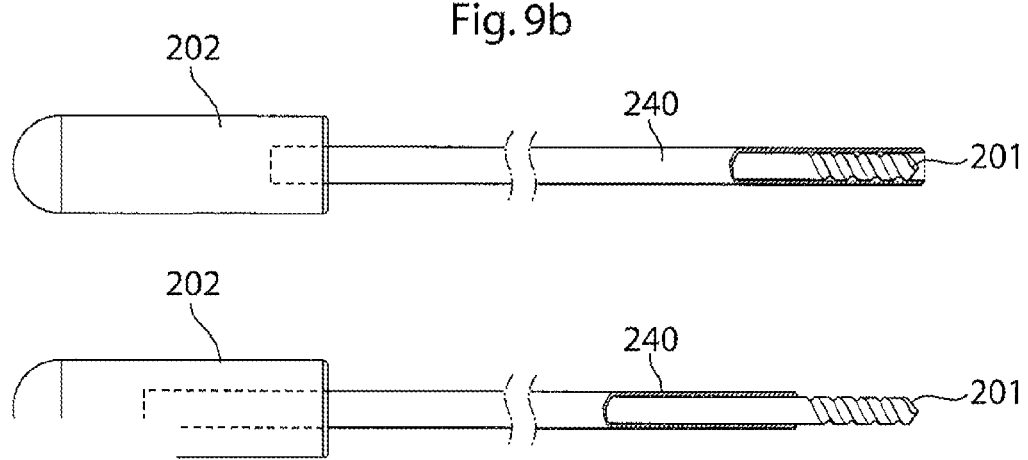
FIG. 9b shows the elongated member in further detail.

FIG. 9b shows the drilling member in further detail, first in a state in which the protective sleeve 240 is advanced for covering the drilling member 201 and thereby protecting the organs and tissue of the human body from the drilling member. Below, the drilling member is shown in a second state, in which the protective sleeve 240 is refracted and thereby exposing the drilling member 201 and enabling the drilling member 201 to create a hole in bone.

After the hole has been created along a force transferring member or elongated member, according to any of the embodiments herein, could be inserted through the holes for delivering an action to the hip joint or its surroundings. The force transferring member could be a tubular or solid shaft, or a flexible member such as a wire.

To reach the pelvic bone or the hip joint from the abdominal side, it is conceivable that the surgical instrument is adapted to be bent.

Figure 10A:
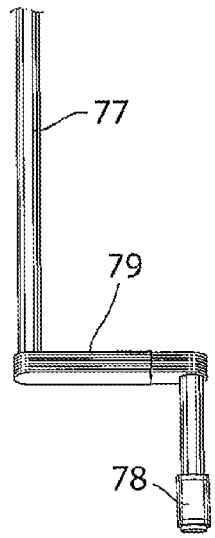
FIG. 10a shows an instrument with a parallel displaced part or section.

FIG. 10a shows the surgical instrument according to a first embodiment wherein the surgical instrument comprises a handling portion 77 and a parallel displaced part or section 79, which increases the reach of the instrument and facilitates the reaching of the pelvic bone or the hip joint through from the abdominal side of the pelvic bone, or through a hole in the pelvic bone from the opposite side from acetabulum.

Figure 10B:
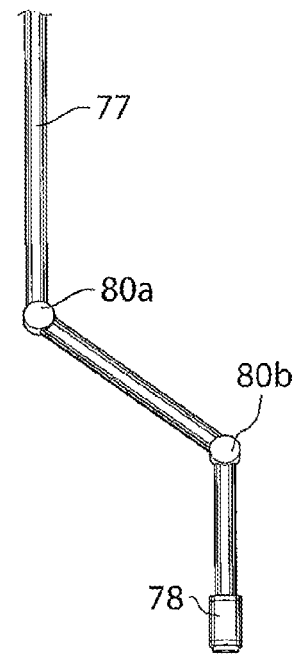
FIG. 10b shows an instrument with two joints.

FIG. 10b shows the surgical instrument according to a second embodiment wherein the surgical instrument comprises two angle adjusting members 80a,b. The angle adjusting members could be adapted to be flexible for adjusting of the angle during surgery or fixed in a preset position.

Figure 10C:
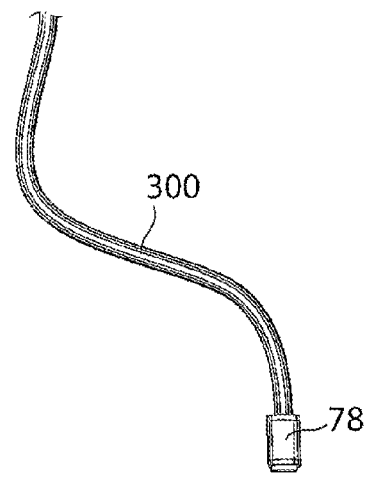
FIG. 10c shows an instrument with a flexible part or section.

FIG. 10c shows the surgical instrument according to a third embodiment wherein the surgical instrument comprises a flexible part or section 300, enabling the surgical instrument to be very precisely adjusted to reach the pelvic bone or the hip joint from the abdominal side of the pelvic bone. The stiffness of said flexible part or section 300 could range from completely flexible to completely stiff to fit the surroundings of the particular operation.

Figure 11:
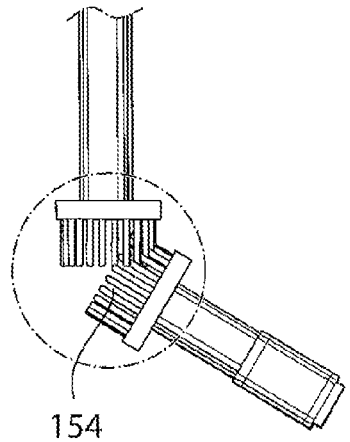
FIG. 11 shows an instrument comprising a worm gear.

FIG. 11 shows the surgical instrument according to a fourth embodiment wherein the surgical instrument is adapted to be bent by means of gearwheels 154. The gearwheel construction can be such that the angled could be changed during the surgery, or it could be adapted to be fixed in a specific angle.

Figure 12:
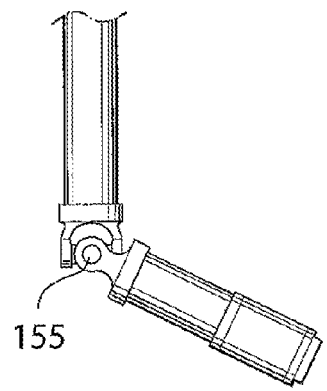
FIG. 12 shows an instrument comprising a universal joint.

FIG. 12 shows the surgical instrument according to a fifth embodiment wherein the surgical instrument is adapted to be bent by means of a universal joint 155. The universal joint construction can be such that the angled could be changed during the surgery, or it could be adapted to be fixed in a specific angle.

Figure 13:
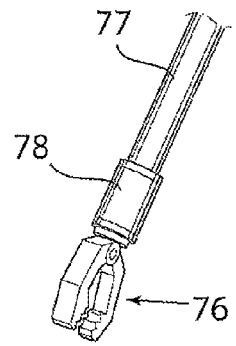
FIG. 13 shows an instrument comprising a gripping member.

FIG. 13 shows the surgical instrument according to a sixth embodiment, wherein the surgical instrument comprises a gripping portion 76 and a handling portion 77. According to the embodiments shown in FIG. 40a the instrument further comprises a rotation element 78 that enables the gripping part 76 to rotate in relation to the handling part 77, however it is equally conceivable that the surgical instrument lacks this rotation element 78.

The surgical instrument is generally adapted to assist the surgeon in a surgical or laparoscopic method of operating hip joint osteoarthritis. Embodiments of the surgical instrument for performing specific task will now be described with reference to the accompanying drawings.

FIG. 14 shows the surgical instrument adapted for a first application wherein said instrument is an instrument for creating a hole 18, 20 in the pelvic bone 9. According to a first embodiment, the instrument comprises a driving member 21a, b. The driving member 21a,b could be a shaft, a rod, a belt, a chain or any other element suitable for transferring force or torque. The instrument also comprises a bone contacting organ 22 which is adapted to create the hole 18, 20 in the pelvic bone 9. The bone contacting organ 22 could have a sawing, drilling or milling effect using sharp objects; it is furthermore conceivable that said bone contacting organ 22 creates a hole using water, abrasive fluids, laser or radiation. The instrument also comprises an operating device 23a adapted to operate the driving member 21a,b. The operating device could comprise an electrical, hydraulic, mechanical, pneumatic or magnetic engine and it could be adapted to create a rotating, oscillating, vibrating or repetitive movement.

FIG. 15 shows the surgical instrument adapted for a first application wherein said instrument is an instrument for creating a hole 18, 20 in the pelvic bone 9 according to a second embodiment in which the operating device 23b is placed in direct connection with the bone contacting organ 22. In this case the operating device 23b also serves as driving member. In this construction a handle portion 24 could be attached to the instrument, facilitating the surgeons handling of said surgical instrument. To improve the reach of the surgical instrument the handle portion 24 could be attached perpendicular to the hole-creating direction 25 of the surgical instrument, it is furthermore conceivable that the handle portion 24 is bent by means of a parallel displaced part or section, a fixed angle, an adjustable angle or a flexible part or section.

FIG. 16 shows the surgical instrument adapted for a first application wherein said instrument is an instrument for creating a hole 18, 20 in the pelvic bone 9 according to a third embodiment wherein the instrument further comprises a parallel displaced part or section 26. The parallel displaced part or section 26 improves the reach of the instrument and enables the creation of a hole 18 in the pelvic bone 9 from the opposite side from acetabulum 8. According to the embodiment shown in FIG. 16 the parallel displaced part or section 26 has a telescopic function by means of the parallel displaced part or section 26 being divided in to a first and second part 27a, b, wherein the second part 27b can slide in and out of the first part 27a.

FIG. 17 shows the surgical instrument adapted for a first application wherein said instrument is an instrument for creating a hole 18, 20 in the pelvic bone 9 according to a fourth embodiment wherein said instrument comprises a driving member 28a,b,c with two angle adjusting members 29a,b. The angle adjusting members 29a,b could be adjustable for varying the angle of said driving member 28a,b,c or fixed in an angle suitable for creating a hole in the pelvic bone 9 from the opposite side from acetabulum 8. In another embodiment (not shown) the part of the driving member 28c in connection with the bone contacting organ 22 could be very short enabling the instrument to operate very close to the pelvic bone 9 when creating a hole 18 in said pelvic bone 9.

FIG. 18 shows the surgical instrument adapted for a first application wherein said instrument is an instrument for creating a hole 18, 20 in the pelvic bone 9 according to a fifth embodiment wherein the driving member 30 is flexible, enabling said driving member 30 to be very precisely adjusted to create a hole 18 in the pelvic bone 9 of the patient. The stiffness of said driving member 30 could range from completely flexible to completely stiff to fit the surroundings of the particular operation.

Figure 19A:
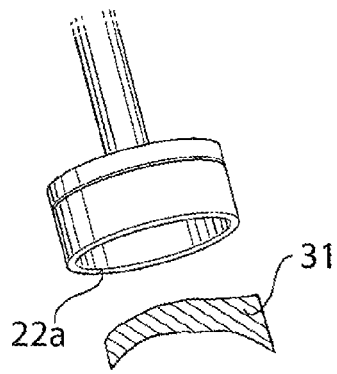
FIG. 19a shows an instrument adapted to create a hole in the pelvic bone in further detail.

FIG. 19a shows the bone contacting organ according to a first embodiment wherein the bone contacting organ 22a is adapted to create a bone plug 31. The bone plug 31 could be adapted to be replaced into said hole 18 after the surgical or laparoscopic steps performed in the hip joint has been concluded.

Figure 19B:
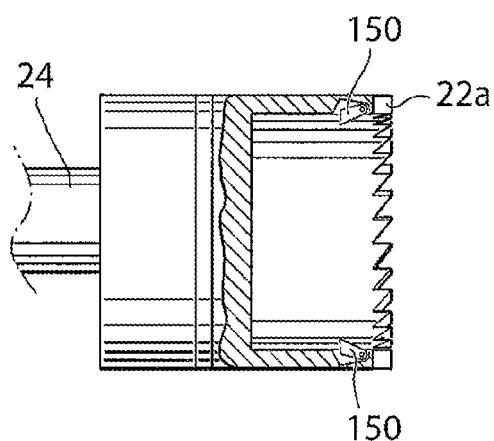
FIG. 19b shows an instrument adapted to create a hole in the pelvic bone in further detail.

FIG. 19b shows the bone contacting organ according to the first embodiment in section wherein the bone contacting organ 22a is adapted to create a bone plug 31. According to this embodiment the instrument further comprises at least one holding member 150 for holding said bone plug in place after it has been removed from the pelvic bone of the human patient.

Figure 20:
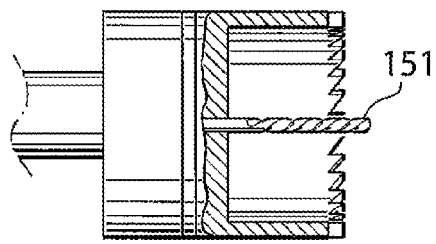
FIG. 20 shows an instrument adapted to create a hole in the pelvic according to another embodiment.

FIG. 20 shows the surgical instrument adapted for a first application wherein said instrument is an instrument for creating a hole 18, 20 in the pelvic bone 9 according to a sixth embodiment wherein said instrument comprises a stabilizing drill 151 adapted to stabilize the instrument when creating said hole in the pelvic bone from the opposite side from acetabulum.

Figure 21:
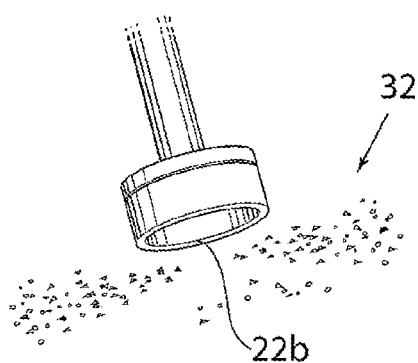
FIG. 21 shows an instrument adapted to create a hole in the pelvic according to another embodiment.

FIG. 21 shows the bone contacting organ according to a second embodiment wherein the bone contacting organ 22b is adapted to create small pieces of bone 32 when creating said hole 18 in the pelvic bone 9. The small pieces of bone 32 could be transported from the area and out of the body using vacuum power or a hydraulic transport system.

Figure 22:
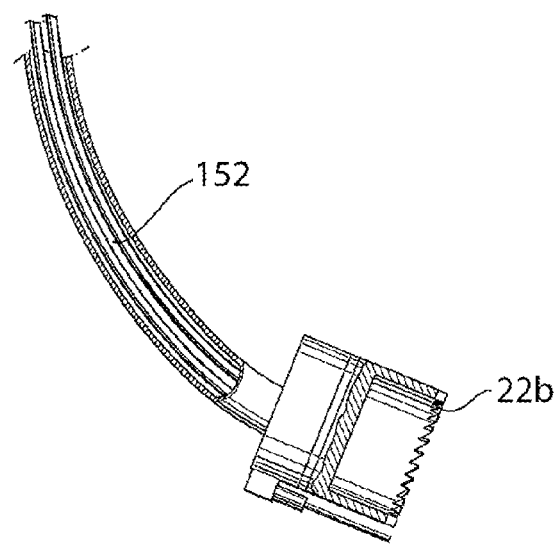
FIG. 22 shows an instrument adapted to create a hole in the pelvic according to another embodiment.

FIG. 22 shows a pneumatic, vacuum powered or a hydraulic transport system 152 for transport of said small pieces of bone. The same system 152 or an additional one could be for rinsing or cooling purposes when creating said hole in the pelvic bone 9.

Figure 23:
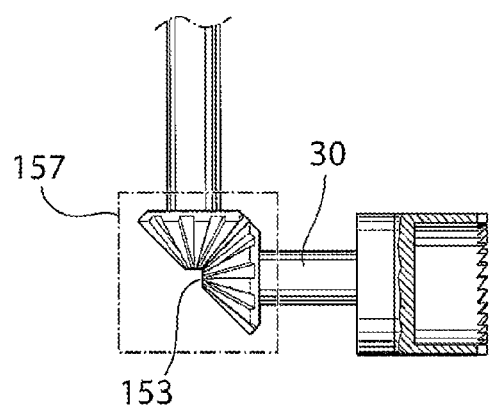
FIG. 23 shows an instrument adapted to create a hole in the pelvic bone comprising two gear wheels.

FIG. 23 shows the surgical instrument adapted for a first application wherein said instrument is an instrument for creating a hole 18, 20 in the pelvic bone 9 according to a seventh embodiment, wherein the driving member 30 comprises at least one worm gear 153 which enables the driving member 30 to be angled. It is also conceivable that said angle could be adjustable in which case said worm gear has a radius (not shown).

Figure 24:
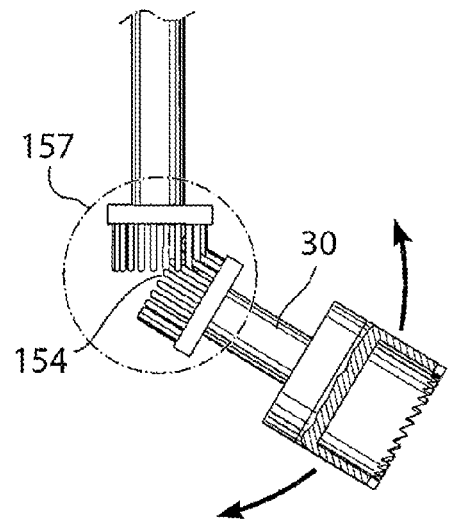
FIG. 24 shows an instrument adapted to create a hole in the pelvic bone comprising a worm gear.

FIG. 24 shows the surgical instrument adapted for a first application wherein said instrument is an instrument for creating a hole 18, 20 in the pelvic bone 9 according to an eight embodiment, wherein the driving member 30 comprises at least one gear wheel 154. In the embodiment shown the two gear wheels 154 is constructed to enable the adjusting of an angle of the driving member 30.

Figure 25:
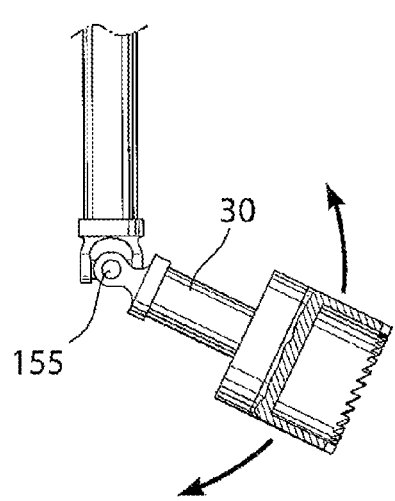
FIG. 25 shows an instrument adapted to create a hole in the pelvic comprising a universal joint.

FIG. 25 shows the surgical instrument adapted for a first application wherein said instrument is an instrument for creating a hole 18, 20 in the pelvic bone 9 according to a ninth embodiment, wherein the driving member 30 comprises at least one universal joint 155, said universal joint enabling the adjusting of an angle of said driving member 30.

Figure 26:
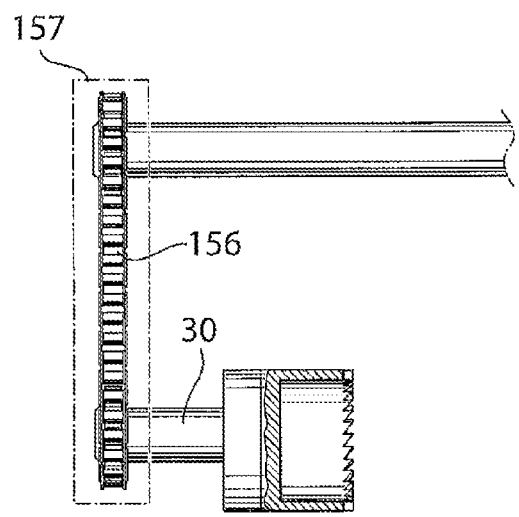
FIG. 26 shows an instrument adapted to create a hole in the pelvic bone comprising a chain.

FIG. 26 shows the surgical instrument adapted for a first application wherein said instrument is an instrument for creating a hole 18, 20 in the pelvic bone 9 according to a tenth embodiment, wherein the driving member 30 comprises at least one chain 156.

According the any of the embodiments above the driving member could comprise a housing 157 shown in FIGS. 23, 24 and 26. Said housing could be adapted to hold a lubricating fluid for lubricating at least a part of said driving member. Said lubricating fluid is preferably a biocompatible lubricating fluid, such as hyaluronic acid.

FIG. 27 shows the surgical instrument adapted for a first application wherein said instrument is an instrument for creating a hole 18, 20 in the pelvic bone 9, according to an embodiment where said operating device comprises an electrical motor 158. Said electrical motor is connected to the driving member 30.

FIG. 28a shows the surgical instrument adapted for a first application wherein said instrument is an instrument for creating a hole 18, 20 in the pelvic bone 9 according to an embodiment wherein said operating device comprises a hydraulic motor 159, hydraulically connected to a hydraulic power source 160 by means of a hydraulic power transport system 161.

FIG. 28b shows the surgical instrument adapted for a first application wherein said instrument is an instrument for creating a hole 18, 20 in the pelvic bone 9 according to an embodiment wherein said operating device comprises a hydraulic motor, but wherein the hydraulic power transport system is located substantially perpendicular to the hole creation direction.

Figure 29:
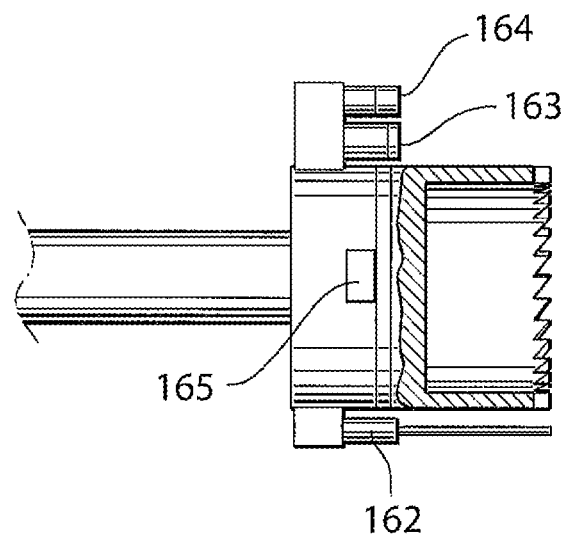
FIG. 29 shows an instrument adapted to create a hole in the pelvic bone in further detail.

FIG. 29 shows the surgical instrument adapted for a first application wherein said instrument is an instrument for creating a hole 18, 20 in the pelvic bone 9 according to an eleventh embodiment wherein said instrument further comprises at least one of: at least one camera 163, at least one light source 164, at least one measurement device for measuring the depth of said hole in the pelvic bone or at least one torque meter 165 for sensing the torque exerted on the driving member 30 from the connection with the bone contacting organ 22 and the operating device 23.

Figure 30:
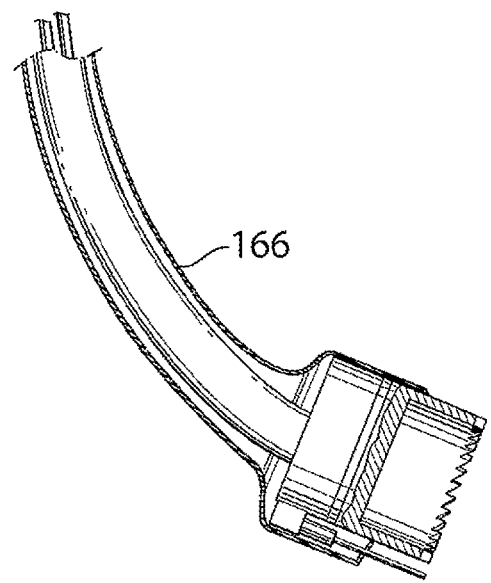
FIG. 30 shows an instrument adapted to create a hole in the pelvic bone comprising a cover.

FIG. 30 shows the surgical instrument adapted for a first application wherein said instrument is an instrument for creating a hole 18, 20 in the pelvic bone 9 according to a twelfth embodiment in which the part of said instrument adapted to be inserted in the human body is covered with a housing 166 for protecting the human body from the parts of the surgical instrument. The housing 166 could be made of a stiff or flexible material and could have an antibacterial surface. Said hosing 166 could be adapted to be used to house the surgical instrument according to any of the embodiments.

Figure 31:
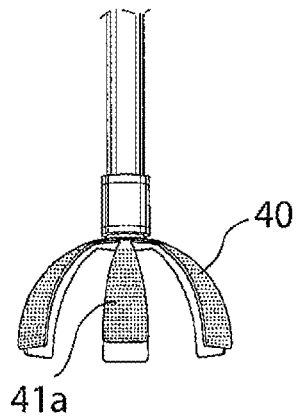
FIG. 31 shows an instrument adapted to ream, in a first position.

FIG. 31 shows the surgical instrument adapted for a second application wherein said instrument is an instrument for holding a mechanical element which according to this embodiment is a reamer adapted to ream the acetabulum or and/or the caput femur. According to one embodiment the reamer could be adapted to be expandable. The expandable reamer comprises at least one reaming blade 40 which comprises a reaming surface 41a,b. Said expandable reamer could be adapted to ream the acetabulum 8, the caput femur 5 or both. In the embodiment where said expandable reamer is adapted to ream the acetabulum 8 said reaming surface 41a is located on the exterior part of the at least one reaming blade 40, whereas in the embodiment when said expandable reamer is adapted to ream the caput femur 5, said reaming surface 41b is located on the interior part of the at least one reaming blade 40. According to a second embodiment said expandable reamer is adapted to ream both the acetabulum and the caput femur, in which case the reamer has reaming surfaces 41a,b both on the exterior and the interior part of the at least one reaming blade 40.

Figure 32:
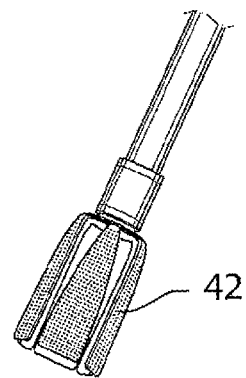
FIG. 32 shows an instrument adapted to ream, in a second position.

FIG. 32 shows the expandable reamer, according to any of the embodiments, wherein the reaming blades 40 can be folded towards a center of the semi-sphere that the expandable reamer produces in its expanded state, shown in FIG. 21. The folding of the reaming blades 40 enables the expandable reamer to be introduced into a hip joint through a hole smaller than the area possible to ream using said expandable reamer.

Figure 33:
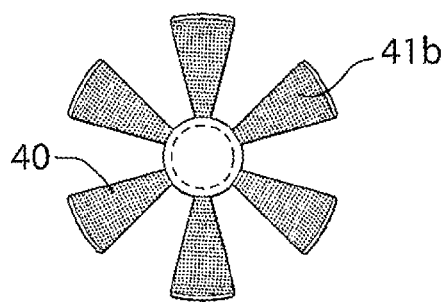
FIG. 33 shows an instrument adapted to ream, from underneath.

FIG. 33 shows the interior said of the expandable reamer with the reaming blades 40. In the embodiment when the expandable reamer is adapted to ream the caput femur said interior side of the at least one reaming blade 40 comprises a reaming surface 41*b*.

Figure 34:
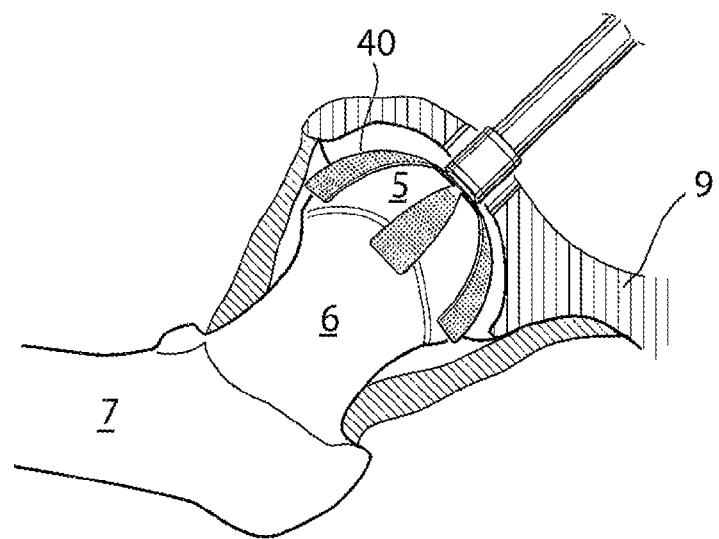
FIG. 34 shows an instrument adapted to ream, when reaming.

FIG. 34 shows the expandable reamer according to any of the embodiments when reaming the acetabulum 8 and/or the caput femur 5. The reamer can be adapted to be operated manually or by means of a rotating, vibrating or oscillating operating device.

FIG. 35 shows the surgical instrument adapted for a second application wherein said instrument is an instrument for reaming the acetabulum or and/or the caput femur, according to a second embodiment wherein the instrument further comprises a parallel displaced part or section 26. The parallel displaced part or section 26 improves the reach of the instrument and enables the reaming of the acetabulum and/or the caput femur through a hole 18 in the pelvic bone 9 from the opposite side from acetabulum 8. According to the embodiment shown in FIG. 16 the parallel displaced part or section 26 has a telescopic function by means of the parallel displaced part or section 26 being divided in to a first and second part 27*a, b*, wherein the second part 27*b* can slide in and out of the first part 27*a*.

FIG. 36 shows the surgical instrument adapted for a second application wherein said instrument is an instrument for reaming the acetabulum or and/or the caput femur, according to a third embodiment wherein said instrument comprises a driving member 28*a,b,c* with two angle adjusting members 29*a,b*. The angle adjusting members 29*a,b* could be adjustable for varying the angle of said driving member 28*a,b,c* or fixed in an angle suitable for reaming the acetabulum and/or the caput femur through a hole in the pelvic bone 9 from the opposite side from acetabulum 8.

FIG. 37 shows the surgical instrument adapted for a second application wherein said instrument is an instrument for reaming the acetabulum or and/or the caput femur, according to a fourth embodiment wherein the driving member 30 is flexible, enabling said driving member 30 to be very precisely adjusted to ream the acetabulum and/or the caput femur through a hole 18 in the pelvic bone 9 of the patient. The stiffness of said driving member 30 could range from completely flexible to completely stiff to fit the surroundings of the particular operation.

FIG. 38 shows a pneumatic, vacuum powered or a hydraulic transport system 152 for transport of the small pieces of bone created when reaming the acetabulum and/or the caput femur. The same system 152 or an additional one could be for rinsing or cooling purposes when reaming the acetabulum and/or caput femur. The shown transport system could be added to the reamer according to any of the embodiments.

Figure 39:
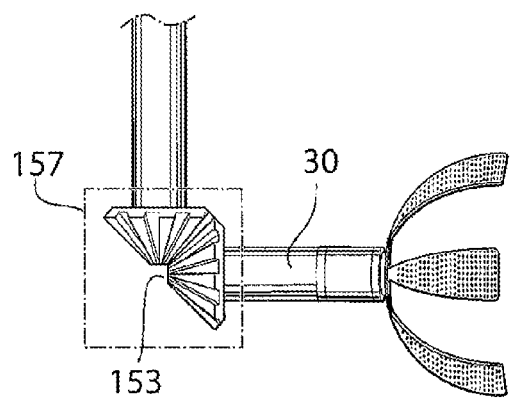
FIG. 39 shows an instrument adapted to ream, comprising two gear wheels.

FIG. 39 shows the surgical instrument adapted for a second application wherein said instrument is an instrument for reaming the acetabulum or and/or the caput femur, according to a fifth embodiment, wherein the driving member 30 comprises at least one worm gear 153 which enables the driving member 30 to be angled. It is also conceivable that said angle could be adjustable in which case said worm gear has a radius (not shown).

Figure 40:
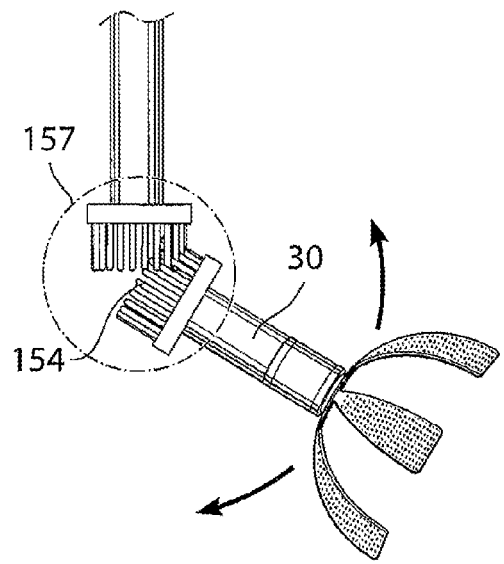
FIG. 40 shows an instrument adapted to ream, comprising a worm gear.

FIG. 40 shows the surgical instrument adapted for a second application wherein said instrument is an instrument for reaming the acetabulum or and/or the caput femur, according to an sixth embodiment, wherein the driving member 30 comprises at least one gear wheel 154. In the embodiment shown the two gear wheels 154 is constructed to enable the adjusting of an angle of the driving member 30.

Figure 41:
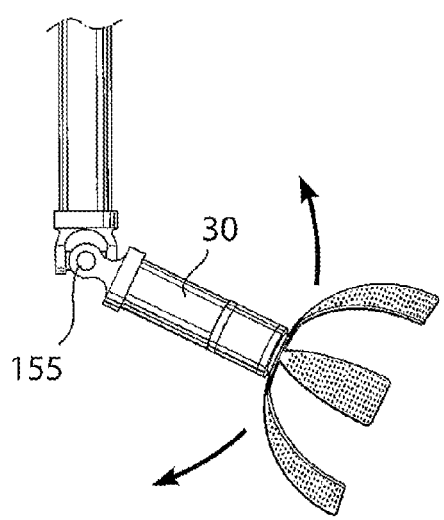
FIG. 41 shows an instrument adapted to ream, comprising a universal joint.

FIG. 41 shows the surgical instrument adapted for a second application wherein said instrument is an instrument for reaming the acetabulum or and/or the caput femur, according to a seventh embodiment, wherein the driving member 30 comprises at least one universal joint 155, said universal joint enabling the adjusting of an angle of said driving member 30.

Figure 42:
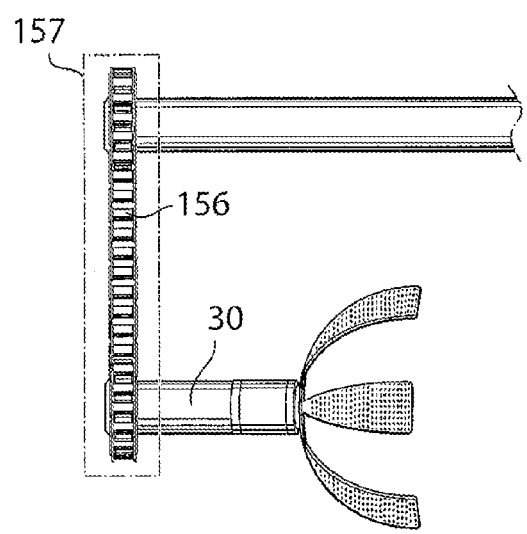
FIG. 42 shows an instrument adapted to ream, comprising a chain.

FIG. 42 shows the surgical instrument adapted for a second application wherein said instrument is an instrument for reaming the acetabulum or and/or the caput femur, according to an eight embodiment, wherein the driving member 30 comprises at least one chain 156.

According the any of the embodiments above the driving member could comprise a housing 157 shown in FIGS. 23, 24 and 26. Said housing could be adapted to hold a lubricating fluid for lubricating at least a part of said driving member. Said lubricating fluid is preferably a biocompatible lubricating fluid, such as hyaluronic acid.

FIG. 43 shows the surgical instrument adapted for a second application wherein said instrument is an instrument for reaming the acetabulum and/or the caput femur, according to an embodiment where said operating device comprises an electrical motor 158. Said electrical motor is connected to the driving member 30.

FIG. 44 shows the surgical instrument adapted for a second application wherein said instrument is an instrument for reaming the acetabulum and/or the caput femur, according to an embodiment wherein said operating device comprises a hydraulic motor 159, hydraulically connected to a hydraulic power source 160 by means of a hydraulic power transport system 161.

FIG. 45 shows the surgical instrument adapted for a second application wherein said instrument is an instrument for reaming the acetabulum or and/or the caput femur, according to an embodiment wherein said operating device comprises a hydraulic motor, but wherein the hydraulic power transport system is located substantially perpendicular to the hole creation direction.

Figure 46:
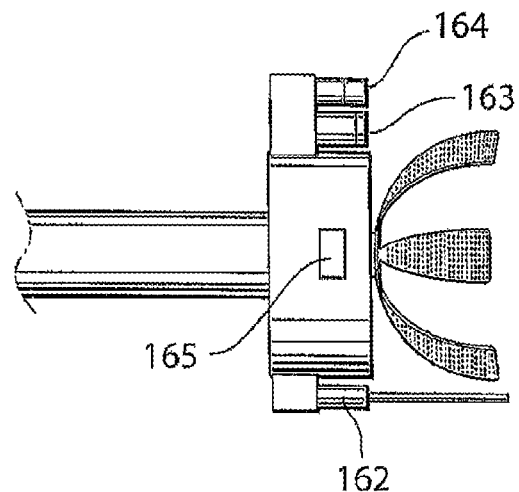
FIG. 46 shows an instrument adapted to ream according to another embodiment.

FIG. 46 shows the surgical instrument adapted for a second application wherein said instrument is an instrument for reaming the acetabulum or and/or the caput femur, according to a ninth embodiment wherein said instrument further comprises at least one of: at least one camera 163, at least one light source 164, at least one measurement device for measuring the depth of said hole in the pelvic bone or at least one torque meter 165 for sensing the torque exerted on the driving member 30 from the connection with the reaming organ and the operating device 23.

Figure 47:
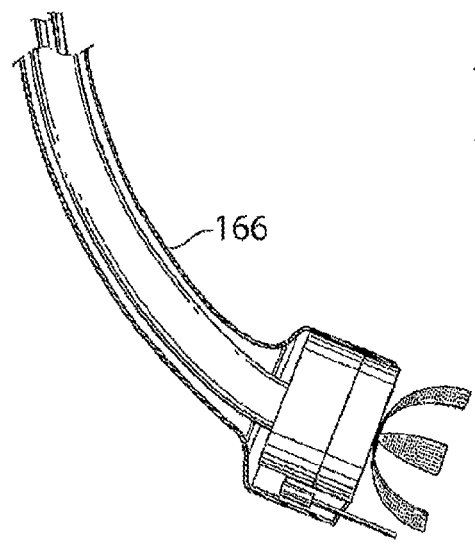
FIG. 47 shows an instrument adapted to ream, comprising a cover.

FIG. 47 shows the surgical instrument adapted for a second application wherein said instrument is an instrument for reaming the acetabulum or and/or the caput femur, according to a tenth embodiment in which the part of said instrument adapted to be inserted in the human body is covered with a housing 166 for protecting the human body from the parts of the surgical instrument, and the surgical instrument from the human body. The housing 166 could be made of a stiff or flexible material and could have an antibacterial surface. Said hosing 166 could be adapted to be used to house the surgical instrument according to any of the embodiments.

Figure 48:
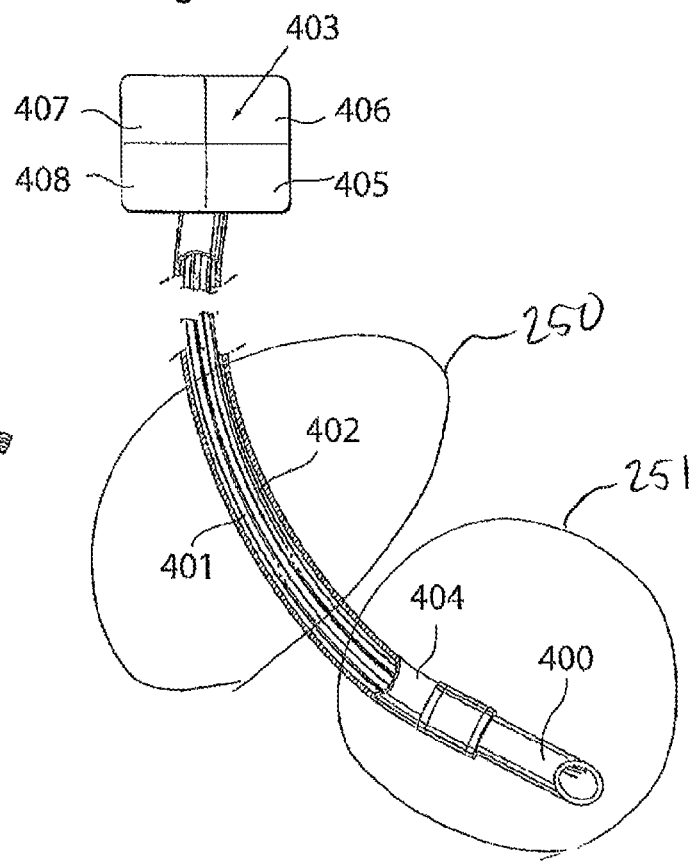
FIG. 48 shows an instrument adapted for flushing, cooling and/or sucking.

FIG. 48 shows the surgical instrument adapted for a third, a fourth and/or a fifth application wherein said instrument is an instrument for flushing, cooling and/or sucking an affected area during an operation for treating hip joint osteoarthritis in a human patient. A member for flushing, cooling and/or sucking 400 is positioned on the proximal part of a hydraulic or pneumatic transportation system 404 comprising one pressure tube 401 and one suction tube 402. In the application where the surgical instrument is used for flushing only, it is conceivable that the hydraulic or pneumatic transportation system 404 only comprises a pressure tube. Furthermore the surgical instrument according to the third application comprises a unit 403 that could comprise at least one of a pneumatic or hydraulic pumping device 405, a cooling member 406, a filter device 407 and an energy accumulating or transforming unit 408. The portions of the instruments adapted to be placed in the abdominal area are the abdominal portions 250, and the portions adapted to at least partially be placed inside of the pelvic bone is the pelvic portions 251 throughout this application.

Figure 49:
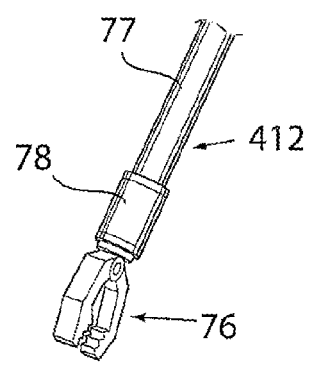
FIG. 49 shows an instrument for gripping or handling.

FIG. 49 shows the surgical instrument adapted for a sixth application, wherein said instrument is an instrument comprising a mechanical element adapted to insert a prosthesis, a prosthetic parts or parts needed to create or provide a hip joint surface, according to a first embodiment wherein the surgical instrument comprises a gripping portion 76 and a handling portion 77. According to the embodiments shown in FIG. 49 the instrument further comprises a rotation element 78 that enables the gripping part 76 to rotate in relation to the handling part 77, however it is equally conceivable that the surgical instrument lacks this rotation element 78.

According to other embodiments the mechanical element comprises a prosthesis or prosthetic part for insertion in the human body.

Figure 50:
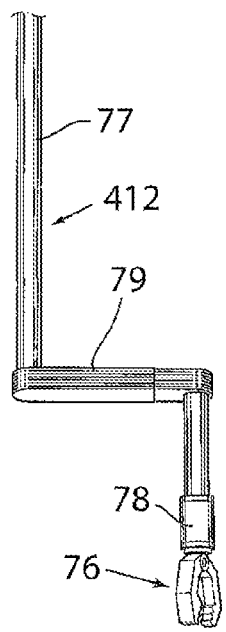
FIG. 50 shows an instrument for gripping or handling, comprising a parallel displaced part or section.

FIG. 50 shows the surgical instrument adapted for a sixth application, wherein said instrument is an instrument adapted to insert a prosthesis, prosthetic parts or parts needed to create or provide a hip joint surface, according to a second embodiment. According to this embodiment the surgical instrument 412 further comprises a parallel displaced section 79, which increases the reach of the surgical instrument 412 and facilitates the reaching of the hip joint through a hole in the pelvic bone from the opposite side from acetabulum.

Figure 51:
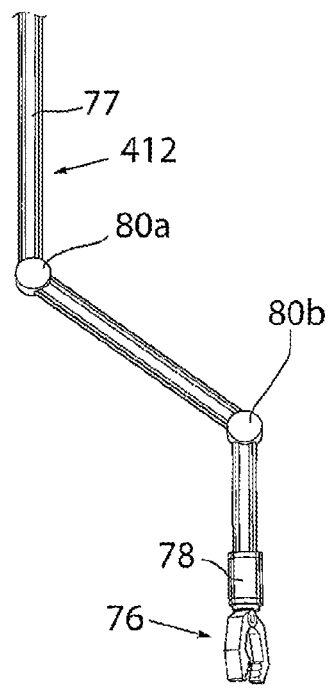
FIG. 51 shows an instrument for gripping or handling, comprising two joints.

FIG. 51 shows the surgical instrument adapted for a sixth application, wherein said instrument is an instrument adapted to insert a prosthesis, prosthetic parts or parts needed to create or provide a hip joint surface, according to a third embodiment. According to this embodiment the surgical instrument 412 further comprises two angle adjusting members 80*a,b*. The angle adjusting members could be adjustable for varying the angle of said gripping part 76 in relation to the handling portion 77, or fixed in an angle suitable for creating operating in a hip joint through a hole in the pelvic bone from the opposite side from acetabulum 8.

Figure 52:
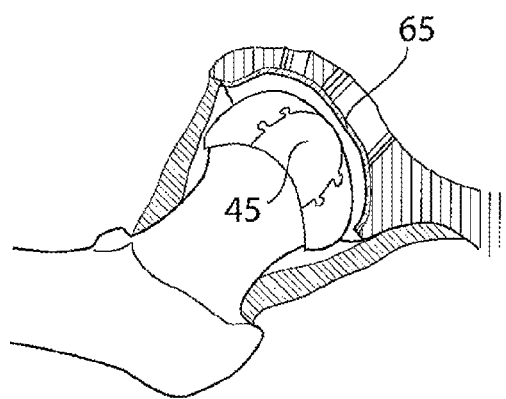
FIG. 52 shows the hip joint in section.

FIG. 52 shows the hip joint in section after the artificial caput femur surface 45, and the artificial acetabulum surface 65 have been provided.

Figure 53:
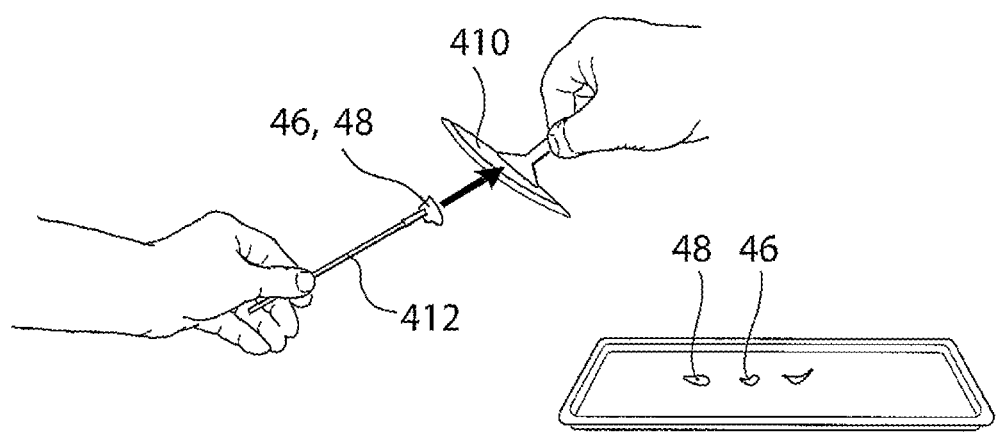
FIG. 53 shows the insertion of prosthetic parts is a surgical method.

FIG. 53 shows the surgical instrument adapted for a sixth application, wherein said surgical instrument 412 is a surgical instrument 412 adapted to insert a prosthesis, prosthetic parts 46, 48 or parts needed to create or provide a hip joint surface when being used by a surgeon to insert a prosthesis, prosthetic parts 46, 48 or parts needed to create or provide a hip joint surface through an opening in said human body.

Figure 54:
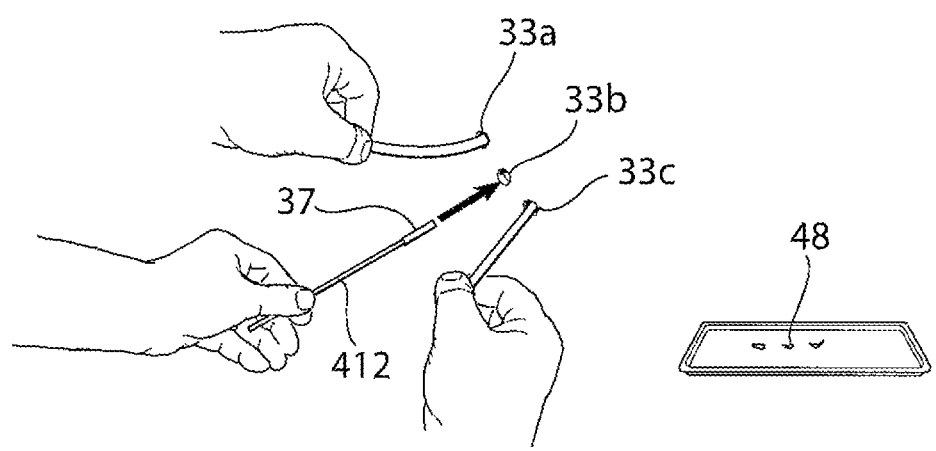
FIG. 54 shows the insertion of prosthetic parts is a laparoscopic method.

FIG. 54 shows a prosthesis, prosthetic parts 48 or parts needed to create or provide a hip joint surface inserted through laparoscopic trocars 33*a,b,c*, through a small incision according to a laparoscopic method. The artificial hip joint surface parts 48 or the artificial caput femur surface parts 46 are adapted to be connected to each other after the insertion to form an artificial hip joint surface.

FIG. 55 shows how an expandable artificial caput femur surface 45 is being inserted through a hole 18 in the pelvic bone 9, using said surgical instrument 412.

FIG. 56*a* shows the hip joint in section with a hole 18 in the pelvic bone 9. An artificial caput femur surface 45 is introduced into the hip joint through the hole 18 in the pelvic bone 9 form the opposite side from acetabulum 8. The artificial caput femur surface parts 46 are connected to each other after insertion into the hip joint to form the artificial caput femur surface 45.

FIG. 56*b* shows the hip joint in section when the artificial caput femur surface parts 46 are connected to each other using the surgical instrument adapted for the sixth application. According to this embodiment the artificial caput femur surface parts 46 are adapted to supply a form fitting 47 that enables the parts to connect to each other without the use of any adhesive or additional mechanical parts. The surgical instrument adapted for the sixth application is adapted to be inserted through a hole 18 in the pelvic bone 9 and connecting said at least two hip joint surface parts 46 to each other. FIG. 56*b* shows the artificial caput femur surface parts, however it is equally conceivable that the artificial hip joint surface parts are artificial acetabulum surface parts. The surgical instrument 413 could comprise at least one gripping member 414, for gripping in the hip joint. The gripping member 414 could be powered by hydraulic, pneumatic or electrical energy. The gripping member 414 or otherwise part being in connection with said artificial hip joint surface parts is in connection with a handling part 416 through a connecting member 415, which could be bent or otherwise adapted to improve the reach of the surgeon for operating in a hip joint through a hole 18 in the pelvic bone 9 of a human patient.

FIG. 56*c* shows the artificial caput femur surface parts 46 with the parts supplying the form fitting 47.

Figure 57:
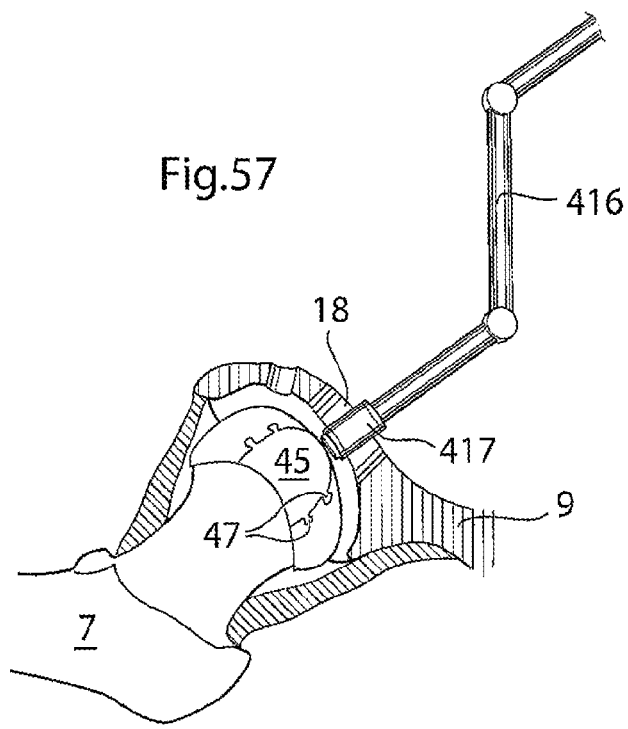
FIG. 57 shows an instrument adapted to fixate a hip joint surface.

FIG. 57 shows the surgical instrument adapted for a seventh application, wherein the surgical instrument 416 is adapted to fixate a hip joint surface 45 to the caput femur 5 through a hole 18 in the pelvic bone 9. According to the embodiment shown in FIG. 57 the surgical instrument 416 is adapted to fixate an artificial caput femur surface, however it is equally conceivable that the surgical instrument 416 is adapted to fixate an artificial acetabulum surface to the pelvic bone 9. The fixation could be done by means of screws, form fitting, welding, adhesive, sprint, band, or other mechanical connecting members. The surgical instrument 416 in FIG. 57 further comprises a member for providing rotational force 417 which could be used to fixate an artificial hip joint surface with screws or other rotation fixation members. The proximal part of the surgical instrument 416 could however also be equipped with a welding electrode, or a tool for fixating artificial hip joint surface using sprint or band.

Figure 58:
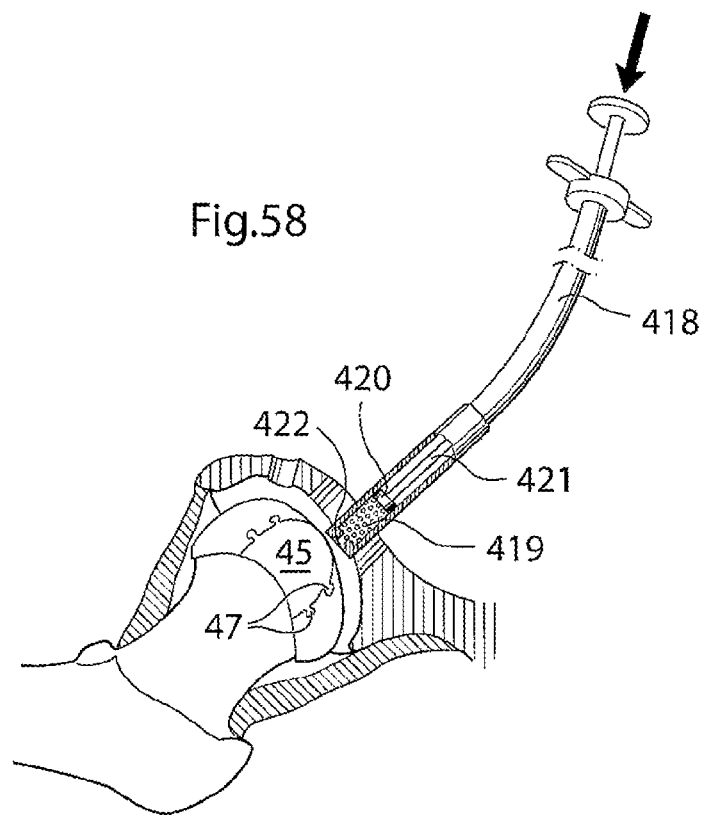
FIG. 58 shows an instrument adapted to inject a fluid into a hip joint.

FIG. 58 shows the surgical instrument adapted for a seventh application, wherein the surgical instrument 416 is adapted to fixate a hip joint surface 45 to the caput femur 5 through a hole 18 in the pelvic bone 9. According to this embodiment the surgical instrument 418 is a surgical instrument 418 adapted to fixate an artificial caput femur surface 45 to the caput femur 5 using bone cement or adhesive. According to this embodiment the surgical instrument 418 comprises a hollow space 419 for housing the fluid 419 such as bone cement or adhesive to be used in the fixation of the artificial hip joint surface. A piston part 420 supplies the pressure to the fluid 419 and pushes it through an injecting tip 422. The piston part 420 is powered or manually operated via a force rod 421 which could be flexible for improved reach.

Figure 59A:
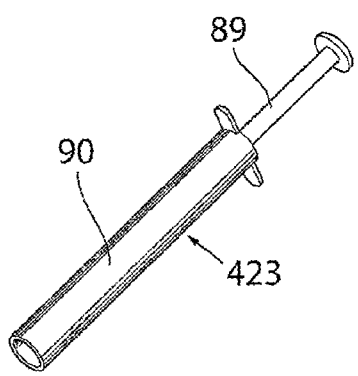
FIG. 59a shows an instrument adapted to insert a mould or a sealing member into a hip joint.

FIG. 59*a* shows the surgical instrument adapted for an eight application wherein the instrument is adapted for placing a mould or a first and/or second sealing member in the hip joint through a hole in the pelvic bone, the femur bone or the hip joint capsule. The mould or sealing member could be used to create an artificial hip joint surface inside of the hip joint. The surgical instrument 423 comprises a piston 89 for transporting said mould or first and/or second sealing member into the hip joint and a tube like element 90 for housing of said mould or first and/or second sealing member.

Figure 59B:
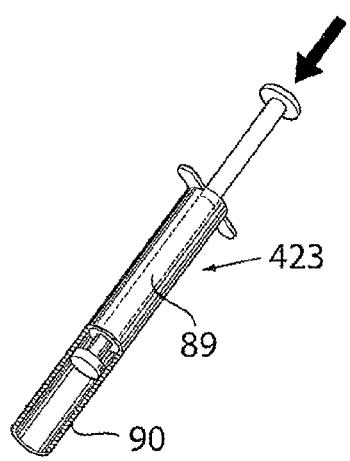
FIG. 59b shows an instrument adapted to insert a mould or a sealing member into a hip joint, in section.
Figure 59C:
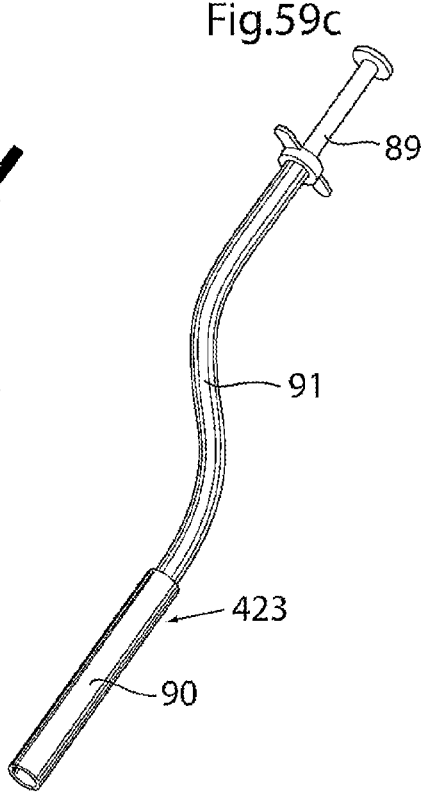
FIG. 59c shows an instrument adapted to insert a mould or a sealing member into a hip joint, comprising a flexible part or section.

FIG. 59b shows a section of the surgical instrument 413 comprising the tube like element 90 for housing of said mould or first and/or second sealing member FIG. 59c shows the surgical instrument 413 according to another embodiment in which the surgical instrument 413 comprises a flexible or bent part 91 improving the reach of the surgical instrument 413. The surgical instrument 413 according to any of the embodiments can be used to place said mould or first or second sealing members inside of the hip joint in any of the ways described in the following embodiments.

Figure 60A:
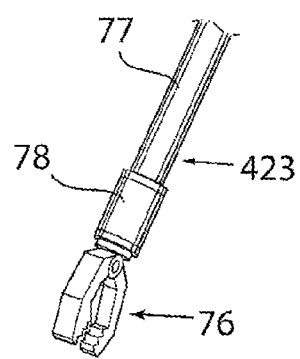
FIG. 60a shows an instrument adapted to insert a mould or a sealing member into a hip joint.

FIG. 60a shows the surgical instrument 423 adapted to insert the mould or first and/or second sealing member in the hip joint, according to a second embodiment. According to this embodiment the surgical instrument 423 comprises a gripping portion 76 and a handling portion 77. According to the embodiments shown in FIG. 60a,b,c the surgical instrument 423 further comprises a rotation element 78 that enables the gripping part 76 to rotate in relation to the handling part 77, however it is equally conceivable that the surgical instrument 423 lacks this rotation element 78.

Figure 60B:
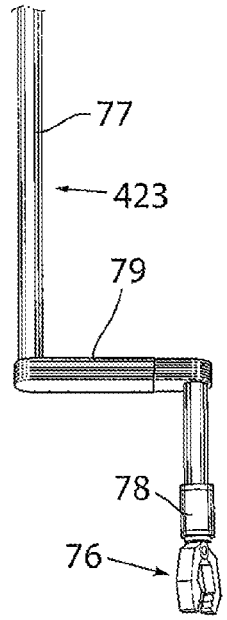
FIG. 60b shows an instrument adapted to insert a mould or a sealing member into a hip joint, comprising a parallel displaced part or section.

FIG. 60b shows the surgical instrument 423 adapted to insert the mould or first and/or second sealing member in the hip joint, according to a third embodiment. According to this embodiment the surgical instrument further comprises a parallel displaced section 79, which increases the reach of the surgical instrument 423 and facilitates the reaching of the hip joint through a hole 18 in the pelvic bone 9, the femoral bone or the hip joint capsule.

Figure 60C:
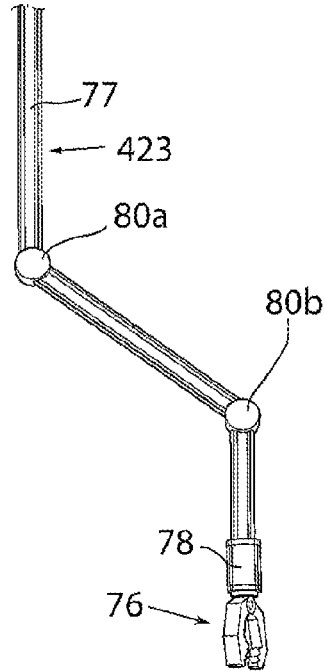
FIG. 60c shows an instrument adapted to insert a mould or a sealing, comprising two joints.

FIG. 60c shows the surgical instrument 423 adapted to insert the mould or first and/or second sealing member in the hip joint, according to a third embodiment. According to this embodiment the surgical instrument 423 further comprises two angle adjusting members 80a,b. The angle adjusting members 80a,b could be adjustable for varying the angle of said gripping part 76 in relation to the handling portion 77, or fixed in an angle suitable for operating in a hip joint through a hole 18 in the pelvic bone 9, the femur bone or the hip joint capsule.

Figure 61:
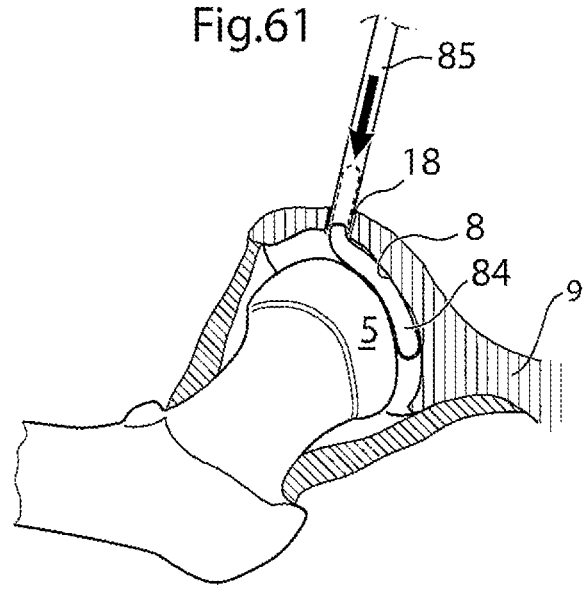
FIG. 61 shows the insertion of a mould or a sealing member, through the pelvic bone.

FIG. 61 shows the hip joint in section wherein a mould or a first sealing member 84 is inserted through a hole 18 in the pelvic bone 9 using an instrument adapted therefor 85. The step of placing said mould or first sealing member 84 can be performed in a surgical, or in a laparoscopic method.

Figure 62:
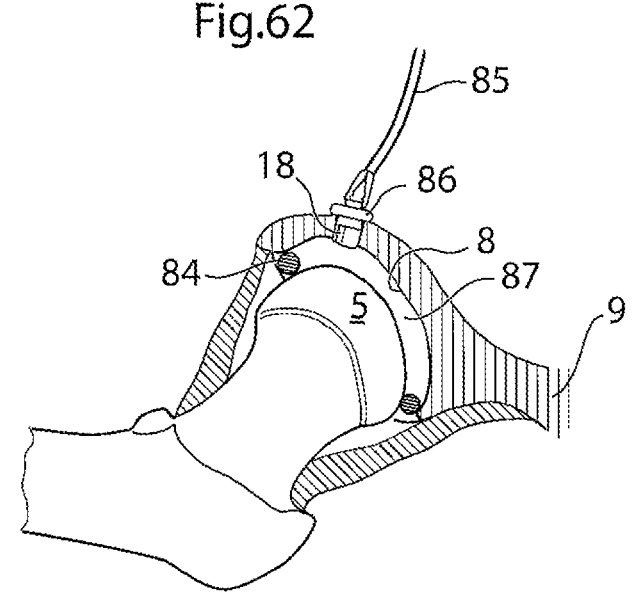
FIG. 62 shows the placing of a second sealing member.

FIG. 62 shows the hip joint in section wherein a second sealing member 86 is inserted through a hole in the pelvic bone 9 in a surgical or a laparoscopic method. The first 84 and second 86 sealing members creates a sealed space 87 between the acetabulum 8 and the caput femur 5 adapted to be used as a mould for providing an artificial acetabulum 65 and/or a caput femur surface 45.

Figure 63A:
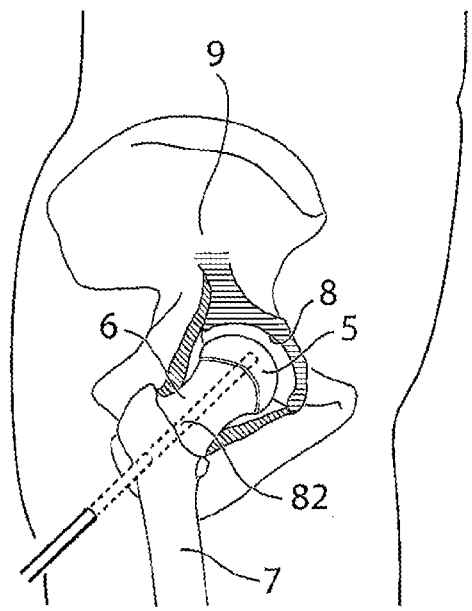
FIG. 63a shows the insertion of a mould or a sealing member, through the femoral bone.
Figure 63B:
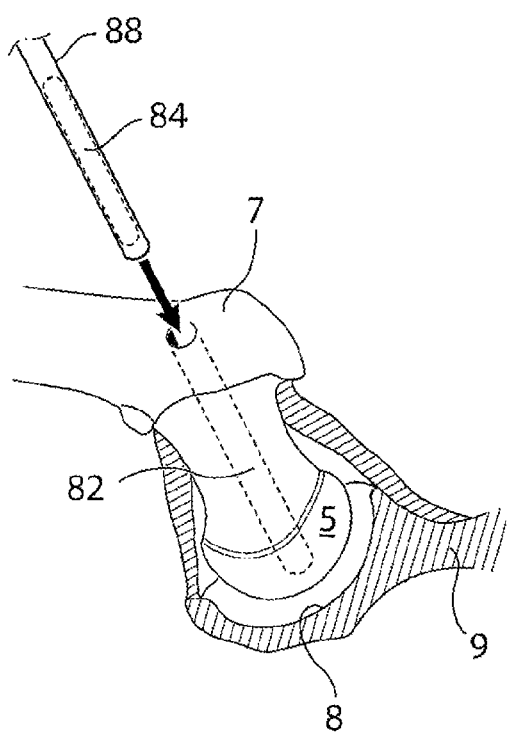
FIG. 63b shows the insertion of a mould or a sealing member, through the femoral bone.
Figure 63C:
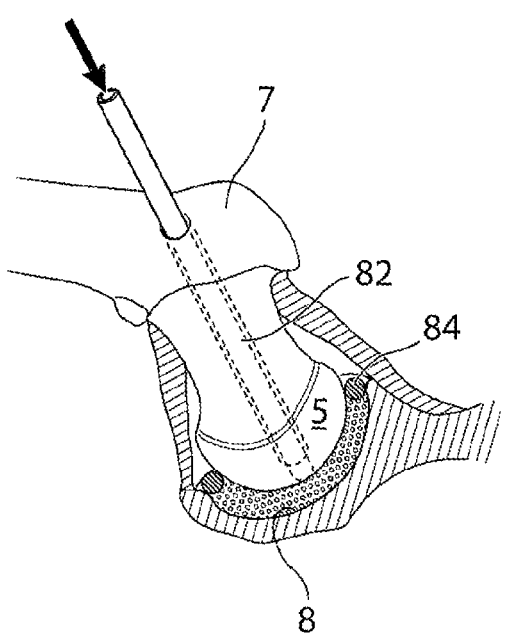
FIG. 63c shows the insertion of a mould or a sealing member, through the femoral bone.

FIG. 63a,b,c shows an alternative approach to placing said mould or first sealing member 84 in the hip joint of a human patient. Said alternative approach comprises the steps of creating a hole 82 in the femur bone 7 following a length axis of the collum femur 6, as shown in FIG. 63a, said hole starting from the lateral side of the thigh, penetrating the cortex of the femur bone 7 and eventually reaching the cortex of the caput femur 5 from the inside thereof, penetrating said cortex and entering into the hip joint. After the creation of the hole 82 in the femur bone 7 the mould or first sealing member 84 is inserted into the hip joint through the hole 82 using a surgical instrument 88 adapted therefor, as shown in FIG. 63c. This approach could also be used for placing a second sealing member 86 in pelvic bone 9 or the femur bone 7 through the hole 82 in the femur bone 7.

FIG. 64 shows a third approach to the placing of a mould or a first sealing member 84 inside of the hip joint. According to this approach the first sealing 84 member is placed in the hip joint through the hip joint capsule 12.

It is furthermore conceivable that the first sealing member 84 is placed in the hip joint using any of the approaches above, whereas the second sealing member 86 is placed in the hip joint using another of the approaches above.

FIG. 65 shows the surgical instrument adapted for a ninth application, wherein the surgical instrument is an injecting member 92 adapted to inject a fluid 93 into a mould or sealed area 81 in the hip joint through a hole 18 in the pelvic bone 9 from the opposite side from acetabulum 8. The injecting member 92 comprises a piston 94 that pushes said fluid 93 into the mould 81.

FIG. 66 shows the hip joint in section wherein an injecting member 92 injects a fluid 93 into a mould 81 or a sealed area in the hip joint through a hole 82 in the femur bone 7. The injecting member 92 comprises a piston 94 that pushes said fluid 93 into the mould 81.

Figure 67:
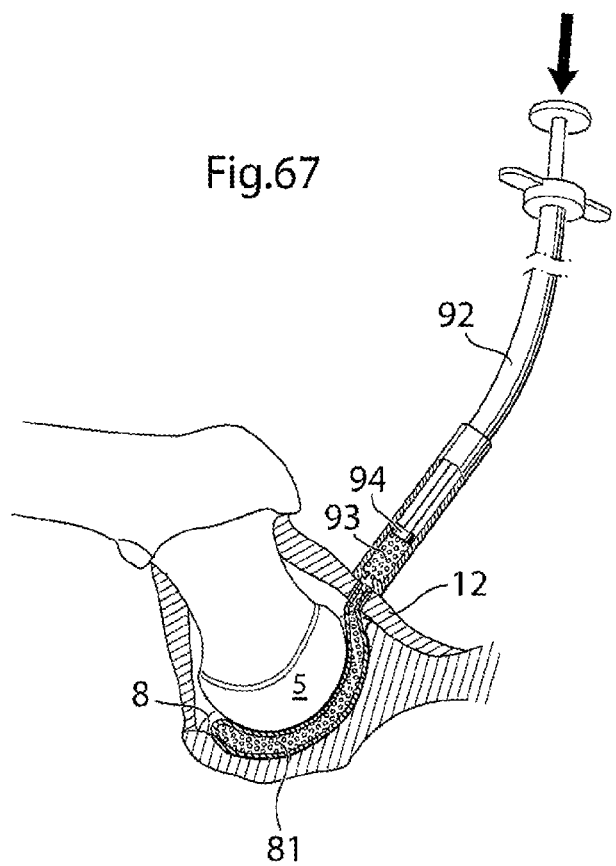
FIG. 67 shows the injection of fluid into a mould, through the hip joint capsule.

FIG. 67 shows the hip joint in section wherein an injecting member injects a fluid 93 into a mould 81 in the hip joint through a hole in the hip joint capsule 12. The injecting member 92 comprises a piston 94 that pushes said fluid 93 into the mould 81. Said fluid 93 being adapted to harden to create a medical device adapted to serve as at least one artificial hip joint surface.

Figure 68:
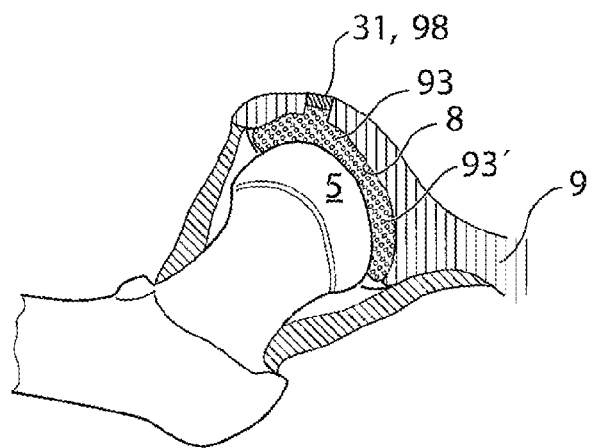
FIG. 68 shows the hip joint in section, after a fluid has been injected.

FIG. 68 shows the hip joint in section wherein the medical device 93' is located between the acetabulum 8 and the caput femur 5 which has been created by the hardening of the fluid 93 adapted to harden. Said medical device is adapted to serve as at least one artificial hip joint surface. The hole in the pelvic bone is preferably sealed with a bone plug 31 or a prosthetic part 98. The mould 81 used to create the medical device 93' has been resorbed by the human body. According to another embodiment the mould used to create the medical device 93' has melted.

Figure 69:
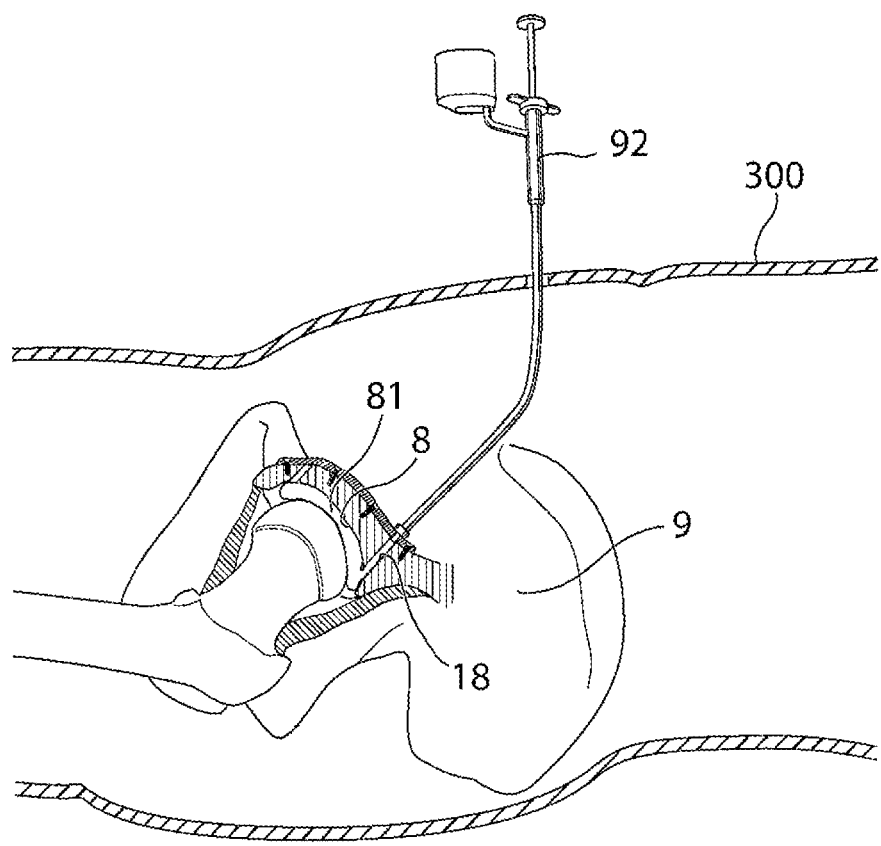
FIG. 69 shows a lateral view of a human patient in section, with an instrument for injecting a fluid.

FIG. 69 shows a lateral section of the human body wherein an injecting member 92 injects a fluid into a mould 81 or a sealed area in the hip joint through a hole 18 in the pelvic bone 9 from the opposite side from acetabulum 8. The injecting member penetrates the skin 300 of the human patient in a surgical or laparoscopic method.

Figure 70:
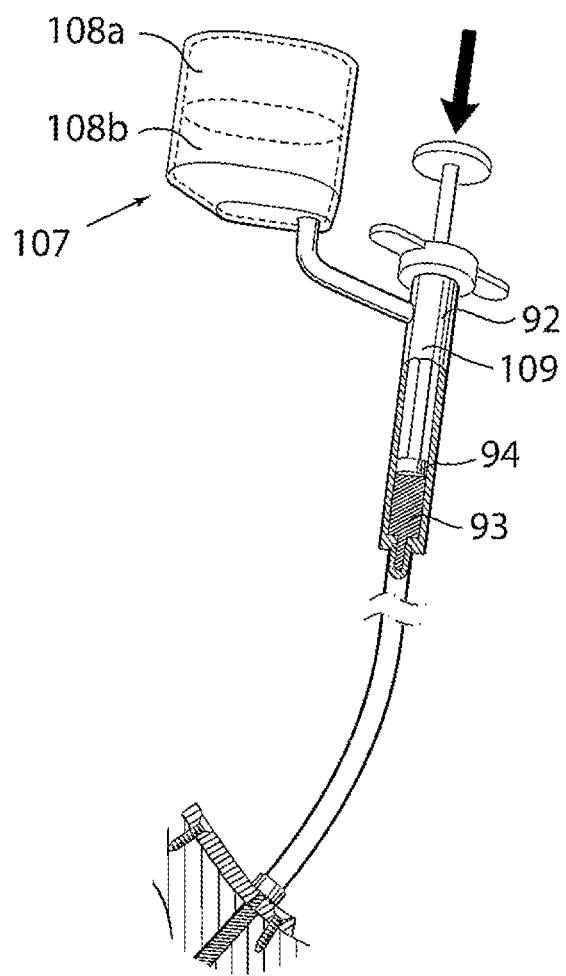
FIG. 70 shows an instrument for injecting a fluid in further detail.

FIG. 70 shows the injecting member 92 according to any of the embodiments above, adapted to inject fluid 93 into a mould 81 in the hip joint. The injecting member 92 could further be adapted to inject material 93 or a fluid 93 into a connecting area between the pelvic bone 9 and a prosthetic part, the pelvic bone 9 and a bone plug 31 or the caput femur 5 and a prosthetic part. Said injecting member 92 comprises a container 107 adapted to hold a fluid 93 for injection. According to a first embodiment said container 107 comprises two compartments 108a,b adapted to hold two different fluids, said fluids being adapted to harden when mixed. In the embodiment when the container 107 is adapted to hold two fluids, it is conceivable that the injecting member 105 further comprises a mixing member 109 wherein said two fluids are being mixed before injection. According to a second embodiment (not shown) said container 107 is adapted to keep said fluid sterile. According to a third embodiment (not shown) said container 107 is adapted to keep said fluid cold or hot and according to a fourth embodiment (not shown) said container 107 is adapted to keep said fluid in a dark environment. Furthermore a combination of the above mentioned embodiments is conceivable.

According to another embodiment (not shown) the fluid is adapted to harden through the mixing with a gas. In which case one of the two compartments is adapted to hold a pressurized gas (such as nitrogen gas) adapted to act as catalyzing agent for the fluid adapted to harden. According to that embodiment the mixing unit 109 is adapted to mix one liquid and one gas fluid. Said first, second or mixed fluid could also be adapted to harden by means of UV-light, thermic change or contact with a body fluid.

According to a tenth application the surgical instrument is adapted to assist in the placing of a bone plug or prosthetic part for sealing the hole in the pelvic bone created to reach the hip joint from the abdominal side of the pelvic bone.

Figure 71A:
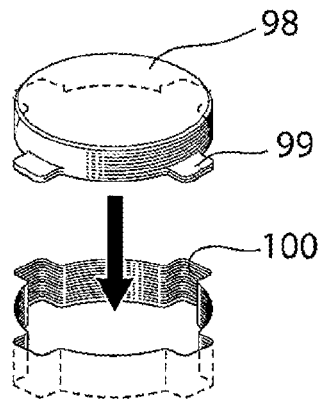
FIG. 71a shows a prosthetic part being used to close a hole in a pelvic bone.

FIG. 71a shows a prosthetic part 98 being inserted into a hole 18 in the pelvic bone 9 from the opposite side from acetabulum 8. According to one embodiment the prosthetic part 98 comprises supporting members 99 adapted to correspond with sections 100 of the hole 18 in the pelvic bone 9. After the prosthetic part 98 has been inserted using said surgical instrument it is rotated so that the supporting members 99 comes in contact with the pelvic bone 9 and can carry the load placed on the acetabulum 8 from weight of the human patient through the contact with the caput femur 5. Said prosthetic part 98 could also be adapted to serve as artificial acetabulum surface 65 according to any of the above mentioned embodiments.

Figure 71B:
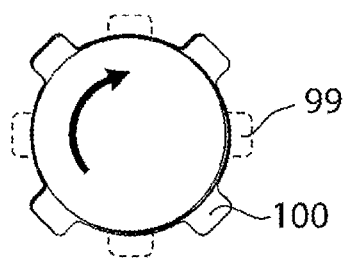
FIG. 71b shows how sections of a prosthetic part is used as support against the edges of the hole in a pelvic bone.

FIG. 71b shows the prosthetic part 98 when rotated to carry the load placed on the acetabulum 8 from weight of the human patient through the contact with the caput femur 5.

Figure 72:
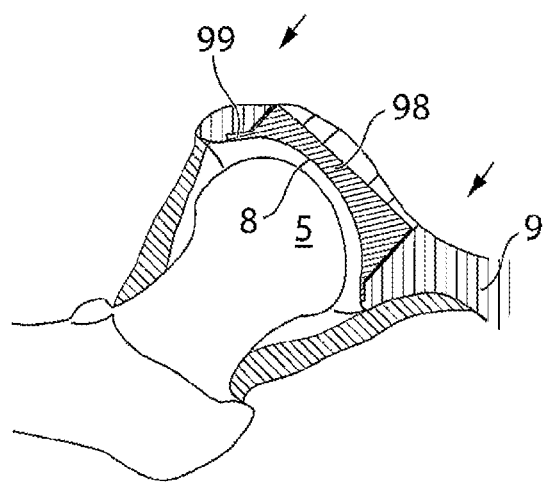
FIG. 72 shows the insertion of a prosthetic part in a hole in a pelvic bone.

FIG. 72 shows the hip joint of a human patient in section wherein the prosthetic part 98 closes the hole 18 in the pelvic bone 9 and carries the load placed on the acetabulum 8 from weight of the human patient through the contact with the caput femur 5 by means of the supporting members 99. The prosthetic part 98 can further be fixated to the pelvic bone 9 by means of bone cement, adhesive, screws, form fitting, welding, sprints, band or some other mechanical connecting member.

Figure 73:
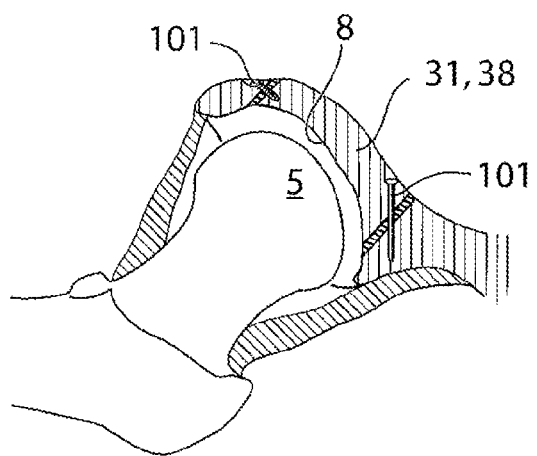
FIG. 73 shows how screws are being used to fixate a bone plug or a prosthetic part in a hole in a pelvic bone of a human patient.

FIG. 73 shows the hip joint of a human patient in section wherein bone plug 31 or prosthetic part 98 is attached to the pelvic bone 9 by means of screws 101 placed from the opposite side from acetabulum 8. The screws 101 are possible to place in different angles depending on reach or need for support.

Figure 74:
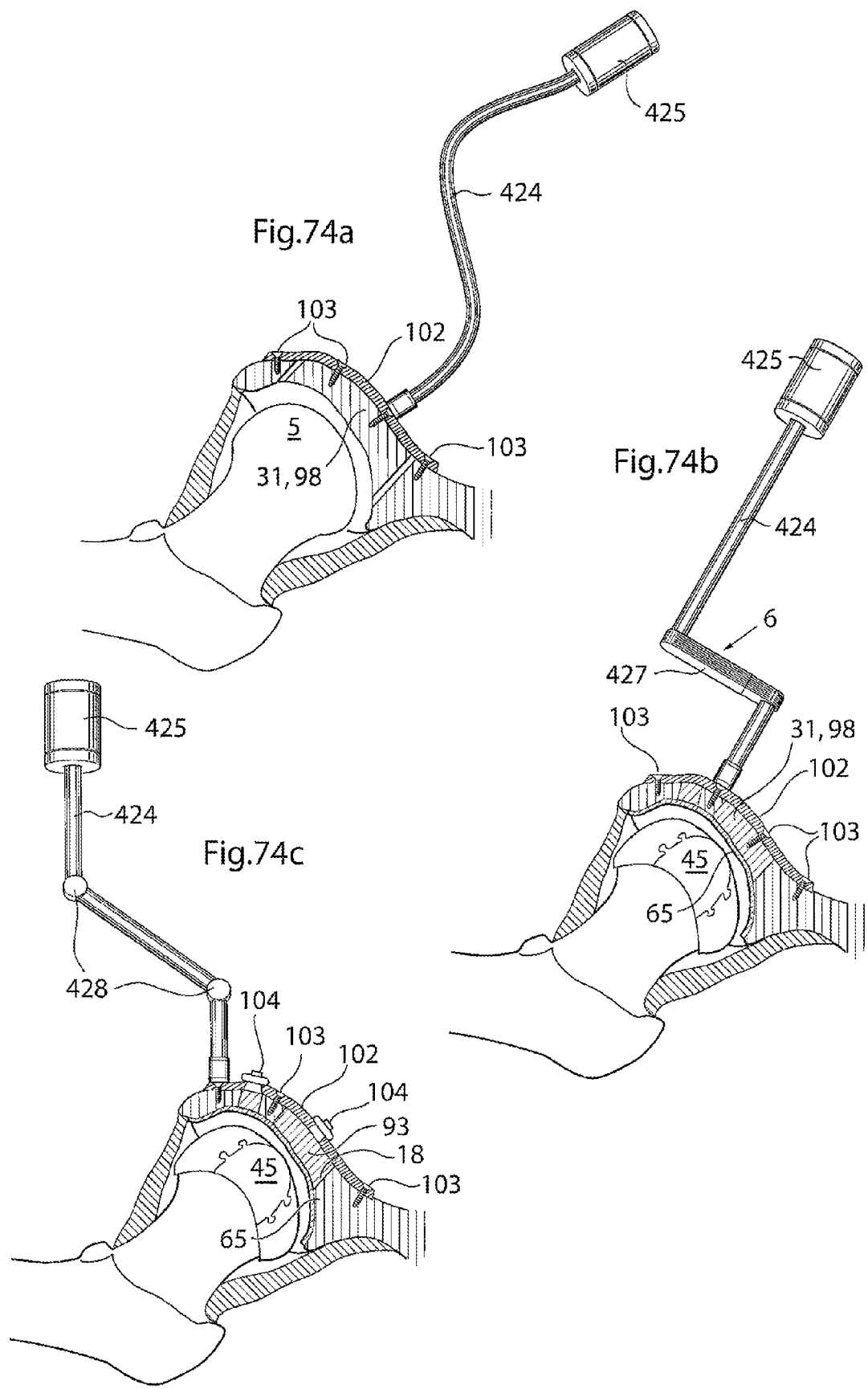
FIG. 74a shows an instrument for fixating fixation members to an area of the pelvic bone.
FIG. 74b shows an instrument for fixating fixation members to an area of the pelvic bone.
FIG. 74c shows an instrument for fixating fixation members to an area of the pelvic bone.

According to an eleventh application the surgical instrument is adapted to assist in the fixation of a bone plug or prosthetic part for sealing the hole in the pelvic bone created to reach the hip joint from the abdominal side of the pelvic bone FIG. 74a shows the hip joint of a human patient in section wherein the surgical instrument 424 is adapted to place screws 103 bone fixating a plate 102 that at least partly covers said bone plug 31 or prosthetic part 98. According to a first embodiment the surgical instrument 424 comprises a flexible part or section 426 that improves the reach of said surgical instrument 424. The surgical instrument 424 further comprises an operating device 425 that supplies rotational force to the surgical instrument for fixating the screws 103.

FIG. 74b shows the surgical instrument 424 according to a second embodiment wherein said surgical instrument comprises a parallel displaced part or section 427 the improves the reach of said surgical instrument 424.

FIG. 74c shows the surgical instrument 424 according to a third embodiment wherein said surgical instrument comprises two angle adjusting members 428 that improves the reach of said surgical instrument 424.

In the above mentioned embodiments the plate 102 and/or the bone plug 31 or prosthetic part 98 are fixated be means of screws 103, however it is equally conceivable that said screws 103 can be replaced or assisted by bone cement, adhesive, form fitting, welding, sprints, band or some other mechanical connecting member.

Figure 75:
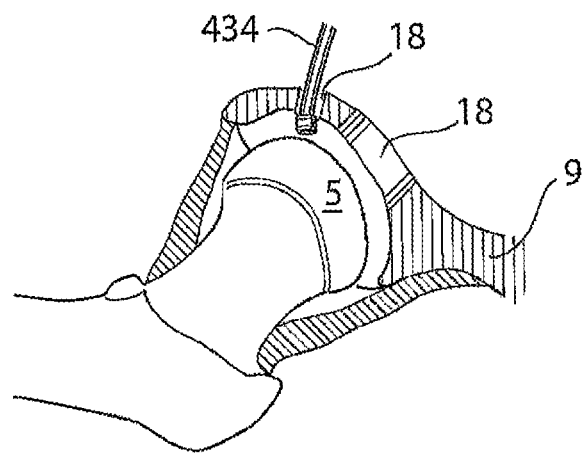
FIG. 75 shows an instrument comprising an arthroscopic camera.

FIG. 75 shows the surgical instrument adapted for an eleventh application wherein said surgical instrument 434 is an arthroscopic camera adapted to be inserted into the hip joint through a hole 18 in the pelvic bone from the abdominal side thereof. It is also conceivable that said surgical instrument 434 is a light source (not shown) or an device for performing x-ray of the hip joint (not shown).

Figure 76:
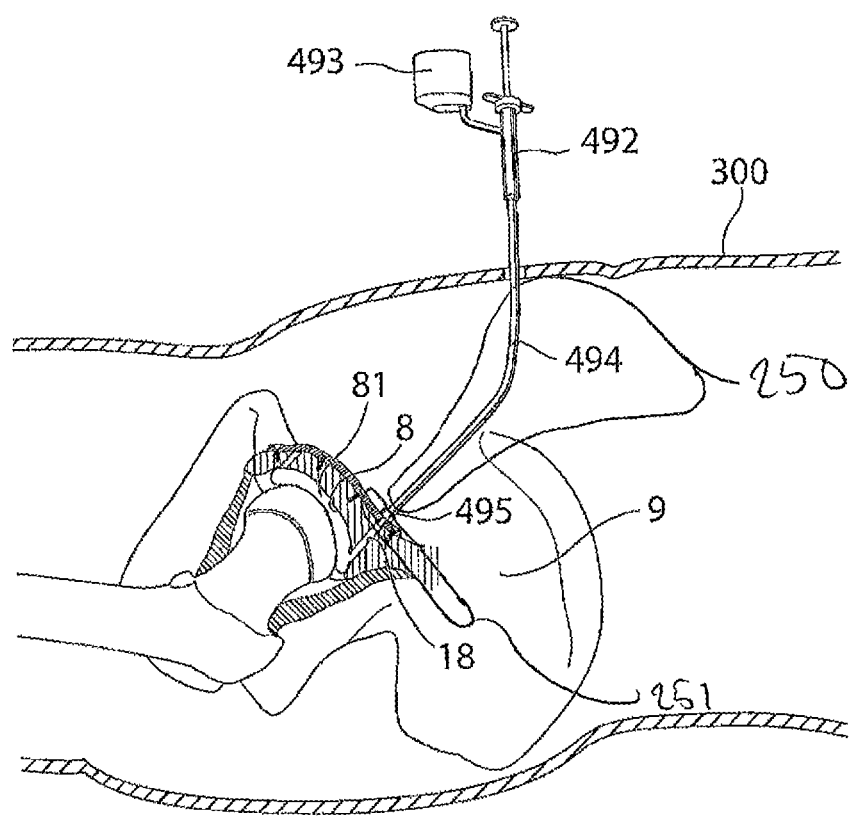
FIG. 76 shows an instrument for injecting a lubricating fluid.

FIG. 76 shows a twelfth application. The surgical instrument 492 is adapted to inject a lubricating fluid into the hip joint, through a hole 18 in the pelvic bone 9. Said lubricating fluid is preferably a biocompatible lubricating fluid such as hyaluronic acid. The surgical instrument 492 comprises a container 493 and a fluid transporting member 494 for transporting said fluid from the container 493 to the injecting member 495, which is the proximal part of said fluid transporting member. The portions of the instruments adapted to be placed in the abdominal area are the abdominal portions 250, and the portions adapted to at least partially be placed inside of the pelvic bone is the pelvic portions 251 throughout this application.

Please note that any embodiment or part of embodiment, feature, method, associated system, part of system described herein may be combined in any way.

The invention claimed is:

1. A surgical instrument for operating hip joint osteoarthritis in a human patient, a hip joint comprising an acetabulum, the acetabulum being a part of a pelvic bone, and a caput femur, the caput femur being a proximal part of a femoral bone, wherein said surgical instrument is adapted to assist in the operating of the hip joint osteoarthritis from an abdominal side of the pelvic bone of said human patient, said surgical instrument comprising:

an abdominal portion insertable through an incision in a skin in an abdominal region and adapted to be placed between the incision in the abdominal region and the pelvic bone when the instrument is in use, and a pelvic portion connected to the abdominal portion, being partially insertable through a hole in the pelvic bone from the abdominal side of the pelvic bone, when the instrument is in use, wherein a portion of the pelvic portion is adapted to operate at least partially in a surgically created hole in the pelvic bone, and a reamer connected to the pelvic portion and being adapted to at least one of ream the acetabulum of said human patient, ream the caput femur of said human patient, and ream both the acetabulum and the caput femur of said human patient, wherein said reamer is expandable, thus allowing said surgical instrument to be inserted through a hole in the pelvic bone smaller than the area possible to ream using said surgical instrument, and an angle adjusting member for adjusting the angle between the reamer and the abdominal portion, and wherein the abdominal portion is more than 100 mm, such that the abdominal portion can reach from the incision in the abdominal region to an area of the hip joint opposite the acetabulum.

2. The surgical instrument according to claim 1, wherein said surgical instrument comprises a bend between said abdominal portion and said pelvic portion.

3. The surgical instrument according to claim 1, further comprising a gripping end for handling of the instrument, wherein said gripping end is connected to the abdominal portion and adapted to remain outside the skin of the patient when the instrument is in use, wherein a portion between the gripping end and a bend is at least 100 mm such that the bend can be placed at the pelvic bone on the opposite side from acetabulum.

4. The surgical instrument according to claim 1, further comprising a gripping end for handling of the instrument, wherein said gripping end is connected to the abdominal portion and adapted to remain outside the skin of the patient when the instrument is in use, wherein a portion between the gripping end and a bend is at least 200 mm such that the instrument can operate inside of the hip joint from the abdominal side of the pelvic bone.

5. The surgical instrument according to claim 1, wherein the surgical instrument is a laparoscopic instrument adapted to be inserted through the skin of the abdominal region through a laparoscopic port.

6. The surgical instrument according to claim 1, wherein the surgical instrument is a laparoscopic instrument introduced into the abdomen and further down to the pelvic bone on the opposite side of the acetabulum and introduced into the hip joint, further comprising a gripping end, placed outside the abdominal wall when in use, and a hip joint end adapted to be placed in an area of the hip joint, wherein the length of said instrument is adapted to reach from the gripping end and into the hip joint via a surgically created hole in the pelvic bone and wherein the longitudinal extension of said instrument comprises at least one bend, for the instrument to reach, when used as a laparoscopic instrument to operate the hip joint, from the gripping end into the abdomen and further down to the pelvic bone on the opposite side of the acetabulum and be introduced into the hip joint through the surgically created hole in the pelvic bone.

7. The surgical instrument according to claim 1, wherein the surgical instrument is a pelvic instrument introduced into the pelvic region and further to the pelvic bone on the opposite side of the acetabulum, and introduced into the hip joint via a surgically created hole in the pelvic bone, further comprising a gripping end, placed outside the skin above the pelvic region when in use, and a hip joint end adapted to be placed in an area of the hip joint, wherein a length of said instrument is adapted to reach from the gripping end and into the hip joint, and wherein a longitudinal extension of said instrument comprises at least one bend, for the instrument to reach, when used as a pelvic instrument to operate the hip joint, from the gripping end into the pelvic region and further down to the pelvic bone on the opposite side of the acetabulum, and introduced into the hip joint through the surgically created hole in the pelvic bone.

8. The surgical instrument according to claim 1, wherein the surgical instrument is a retroperitoneal instrument introduced into the body just above the inguinal region following the pelvic bone down to the opposite side of the acetabulum and thereafter introduced into the hip joint via a surgically created hole in the pelvic bone, further comprising a gripping end, placed outside the skin above the pelvic region when in use, and a hip joint end adapted to be placed in an area of the hip joint, wherein a length of said instrument is adapted to reach from the gripping end and into the hip joint and wherein a longitudinal extension of said instrument comprises at least one bend, for the instrument to reach, when used as retroperitoneal instrument to operate the hip joint, from the gripping end following the pelvic bone and further down to the pelvic bone on an opposite side of the acetabulum and introduced into the hip joint through the surgically created hole in the pelvic bone.

9. The surgical instrument according to claim 1, wherein said instrument further comprises at least one holding portion connected to the pelvic portion, and at least one mechanical element adapted to be fitted to said at least one holding portion of said instrument, wherein said mechanical element is adapted to perform a function during an operation of the hip joint, wherein said mechanical element is adapted to be part of an instrument adapted to be used for at least one of the following functions; drilling, reaming, cooling, heating, flushing, introducing a fluid, sucking, inserting at least one part, connecting at least one part, fixating at least one part, inserting a mould, filling a mould, injecting, lubricating, viewing, optically displaying, placing screws, placing adhesive, and placing bone cement.

10. The surgical instrument according to claim 6, wherein the distance between the gripping end and the bend is at least one of; at least 150 mm, at least 200 mm, at least 300 mm, at least 400 mm, and at least 500 mm.

11. The surgical instrument according to claim 2, wherein said bend is bent with an angle of at least one of; at least 10 degrees, at least 20 degrees, at least 30 degrees, at least 40 degrees, at least 50 degrees, and at least 60 degrees.

12. The surgical instrument according to claim 2, wherein the distance between said bend and the pelvic portion of the instrument is at least one of at least 20 mm, at least 40 mm, at least 60 mm, at least 80 mm, at least 100 mm, at least 120 mm, and at least 140 mm.

13. The surgical instrument according to claim 1, wherein said surgical instrument further comprising at least one camera.

14. The surgical instrument according to claim 1, wherein said surgical instrument further comprising at least one light source.

15. The surgical instrument according to claim 1, wherein said surgical instrument is adapted to at least one of:
   introduce a prosthesis through the hole in the pelvic bone and into the hip joint,
   connect at least two prosthetic parts to each other after insertion into the hip joint,
   fixate an artificial hip joint surface, or a part of an artificial hip joint surface, to the pelvic bone or the femoral bone, and
   place or fixate fixating elements to the pelvic bone or a prosthetic part in the hip region or the pelvic bone region.

16. The surgical instrument according to any one of claims 1, wherein said surgical instrument is adapted to at least one of;
   cool an area of the hip joint or an area of the pelvic bone,
   provide a fluid to an area of the pelvic bone or the hip joint, and
   provide suction to an area of the pelvic bone or an area of the hip joint,
   introduce a mould into the hip joint,
   inject a fluid into a mould placed in the hip joint,
   introduce adhesive into the hip joint,
   inject a lubricating fluid into the hip joint, said surgical instrument comprising at least one container, a fluid injecting member, and a fluid driving member in fluid connection with said fluid injecting member and said at least one container.

* * * * *